(12) United States Patent
Bonnette et al.

(10) Patent No.: US 11,553,942 B2
(45) Date of Patent: Jan. 17, 2023

(54) ACCESSORY DEVICES FOR USE WITH CATHETERS

(71) Applicant: BOSTON SCIENTIFIC SCIMED, INC., Maple Grove, MN (US)

(72) Inventors: Michael J. Bonnette, Minneapolis, MN (US); Michael P. Schrom, Forest Lake, MN (US); Jason T. Anderson, Deephaven, MN (US); David B. Morris, Anoka, MN (US); Debra M. Kozak, Forest Lake, MN (US); Jeffrey Alan Nylund, St. Michael, MN (US); Kenneth R. Larson, Grand Rapids, MN (US); Katherine Stryker Brodeen Routh, Coon Rapids, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 78 days.

(21) Appl. No.: 17/094,679

(22) Filed: Nov. 10, 2020

(65) Prior Publication Data
US 2021/0068861 A1   Mar. 11, 2021

Related U.S. Application Data

(63) Continuation of application No. 15/449,301, filed on Mar. 3, 2017, now Pat. No. 10,828,061.
(Continued)

(51) Int. Cl.
*A61B 17/3203* (2006.01)
*A61B 17/221* (2006.01)
(Continued)

(52) U.S. Cl.
CPC ...... *A61B 17/32037* (2013.01); *A61B 17/221* (2013.01); *A61M 25/0026* (2013.01);
(Continued)

(58) Field of Classification Search
CPC .............. A61M 25/09; A61M 25/0041; A61M 25/0136; A61M 2025/09083;
(Continued)

(56) References Cited

U.S. PATENT DOCUMENTS 5,312,356 A    5/1994  Engelson et al.
6,355,051 B1 *  3/2002  Sisskind ............... A61F 2/0108
                                                        606/200

(Continued)

FOREIGN PATENT DOCUMENTS

EP    0788774 A1    8/1997
EP    1088568 A1    4/2001
(Continued)

OTHER PUBLICATIONS

Invitation to Pay Additional Fees dated Apr. 21, 2017 for International Application No. PCT/US2017/020717.
(Continued)

*Primary Examiner* — Mohamed G Gabr
(74) *Attorney, Agent, or Firm* — Seager, Tufte & Wickhem LLP

(57) ABSTRACT

An accessory device may be used in combination with a thrombectomy catheter. The accessory device may be configured to deflect a distal portion of the thrombectomy catheter and/or disrupt a lesion in a vessel.

17 Claims, 35 Drawing Sheets

Related U.S. Application Data

(60) Provisional application No. 62/396,803, filed on Sep. 19, 2016, provisional application No. 62/303,193, filed on Mar. 3, 2016.

(51) Int. Cl.
  *A61M 25/00* (2006.01)
  *A61M 25/09* (2006.01)
  *A61B 17/00* (2006.01)
  *A61B 17/22* (2006.01)
  *A61M 25/01* (2006.01)

(52) U.S. Cl.
  CPC ..... *A61M 25/09* (2013.01); *A61B 2017/0046* (2013.01); *A61B 2017/22038* (2013.01); *A61B 2017/22079* (2013.01); *A61B 2217/005* (2013.01); *A61M 2025/0177* (2013.01)

(58) Field of Classification Search
  CPC ........... A61M 2025/0915; A61M 2025/09175; A61M 2025/0183; A61M 2025/0063; A61B 17/32037; A61B 2017/22038; A61B 5/6851
  See application file for complete search history.

(56) References Cited

U.S. PATENT DOCUMENTS

| | | |
|---|---|---|
| 6,949,104 B2 | 9/2005 | Griffis et al. |
| 7,048,695 B1 | 5/2006 | Schwager |
| 7,226,433 B2 | 6/2007 | Bonnette et al. |
| 8,998,843 B2 | 4/2015 | Bonnette et al. |
| 9,078,691 B2 | 7/2015 | Morris et al. |
| 2002/0173819 A1 | 11/2002 | Leeflang et al. |
| 2004/0073141 A1 | 4/2004 | Hartley et al. |
| 2005/0240146 A1 | 10/2005 | Nash et al. |
| 2006/0129091 A1 | 6/2006 | Bonnette et al. |
| 2006/0135870 A1 | 6/2006 | Webler |
| 2007/0282303 A1 | 12/2007 | Nash et al. |
| 2008/0004643 A1 | 1/2008 | To et al. |
| 2008/0058839 A1 | 3/2008 | Nobles et al. |
| 2008/0097499 A1 | 4/2008 | Nash et al. |
| 2008/0188831 A1 | 8/2008 | Bonnette et al. |
| 2010/0145259 A1 | 6/2010 | Nash et al. |
| 2014/0155830 A1* | 6/2014 | Bonnette ........... A61M 25/0026 604/150 |
| 2014/0163550 A1 | 6/2014 | Besser et al. |
| 2014/0343457 A1 | 11/2014 | Shekalim et al. |
| 2014/0343595 A1 | 11/2014 | Monstadt et al. |
| 2015/0032138 A1 | 1/2015 | Jenson et al. |
| 2015/0094748 A1 | 4/2015 | Nash et al. |
| 2016/0270814 A1 | 9/2016 | Palme et al. |
| 2018/0000510 A1 | 1/2018 | Nash et al. |
| 2018/0235648 A1 | 8/2018 | Wilke et al. |

FOREIGN PATENT DOCUMENTS

| | | |
|---|---|---|
| EP | 1092396 A2 | 4/2001 |
| EP | 2712559 A2 | 4/2014 |
| WO | 9613295 A1 | 5/1996 |
| WO | 2017152086 A1 | 9/2017 |

OTHER PUBLICATIONS

International Search Report and Written Opinion for Application No. PCT/US2018/018762, 14pages, dated Apr. 20, 2018.

* cited by examiner

ACCESSORY DEVICES FOR USE WITH CATHETERS

CROSS-REFERENCE TO RELATED APPLICATIONS

This application a continuation of U.S. application Ser. No. 15/449,301, filed Mar. 3, 2017, now U.S. Pat. No. 10,828,061; which claims the benefit of priority under 35 U.S.C. § 119(e) of U.S. Provisional Application No. 62/396,803, filed Sep. 19, 2016 and U.S. Provisional Application No. 62/303,193, filed Mar. 3, 2016, the entire disclosures of which are herein incorporated by reference.

TECHNICAL FIELD

The disclosure is directed to accessory devices for use with catheters. More particularly, the disclosure is directed to devices to aid in removing or accelerating the removal of thrombus.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices.

In a first example a thrombectomy catheter may comprise a catheter tube extending from a catheter proximal portion to a catheter distal portion and including a catheter lumen extending between the proximal portion and the distal portion, a high pressure tube extending through the catheter lumen from the catheter proximal portion toward the catheter distal portion, the high pressure tube configured for communication with a fluid source near the catheter proximal portion, a fluid jet emanator in communication with the high pressure tube, the fluid jet emanator having at least one jet orifice for directing at least one fluid jet from said fluid jet emanator through the catheter lumen, an outflow orifice located along a catheter perimeter of the catheter distal portion, an entrainment inflow orifice positioned along the catheter distal portion, and an accessory device disposed within the catheter lumen.

Alternatively or additionally to any of the examples above, in another example, the accessory device may comprise a guidewire having proximal end portion and a distal end portion.

Alternatively or additionally to any of the examples above, in another example, the proximal portion of the guidewire may extend along a longitudinal axis and the distal portion of the guidewire may be configured to extend at an angle to the longitudinal axis.

Alternatively or additionally to any of the examples above, in another example, the angle may be in the range of 10 to 50°.

Alternatively or additionally to any of the examples above, in another example, the angle may be in the range of 15 to 35°.

Alternatively or additionally to any of the examples above, in another example, the guidewire may comprise a bent portion disposed between the proximal end portion and the distal end portion of the guidewire.

Alternatively or additionally to any of the examples above, in another example, the bent portion of the guidewire may be configured to deflect a portion of the catheter tube positioned distal to the bent portion.

Alternatively or additionally to any of the examples above, in another example, when the bent portion is positioned at a first longitudinal location within the catheter lumen, the thrombectomy catheter may have a first sweep coverage and when the bent portion is positioned at a second longitudinal location within the catheter lumen, the second location proximal to the first location, the thrombectomy catheter may have a second sweep coverage greater than the first sweep coverage.

Alternatively or additionally to any of the examples above, in another example, the thrombectomy catheter may further comprise a control handle releasably secured adjacent to a proximal end of the accessory device.

Alternatively or additionally to any of the examples above, in another example, the control handle may comprise a body portion, a slide portion, and a collet portion.

Alternatively or additionally to any of the examples above, in another example, the collet portion may be configured to be releasably secured to the accessory device.

Alternatively or additionally to any of the examples above, in another example, the control handle may be configured to rotate independent of the catheter body.

Alternatively or additionally to any of the examples above, in another example, the accessory device may be configured to rotate with rotation of the control handle.

Alternatively or additionally to any of the examples above, in another example, the bent portion may have a radius of curvature in the range of 1 to 2 millimeters.

Alternatively or additionally to any of the examples above, in another example, the guidewire may have a stiffness that is less than a stiffness of the catheter proximal portion and greater than a stiffness of the catheter distal portion.

In another example, a thrombectomy catheter may comprise a catheter tube extending from a catheter proximal portion to a catheter distal portion and including a catheter lumen extending between the catheter proximal portion and the catheter distal portion, a high pressure tube extending through the catheter lumen from the catheter proximal portion toward the catheter distal portion, the high pressure tube configured for communication with a fluid source near the catheter proximal portion, a fluid jet emanator in communication with the high pressure tube, the fluid jet emanator having at least one jet orifice for directing at least one fluid jet from said fluid jet emanator through the catheter lumen, an outflow orifice located along a catheter perimeter of the catheter distal portion, an entrainment inflow orifice positioned along the catheter distal portion, and an accessory device disposed within the catheter lumen.

Alternatively or additionally to any of the examples above, in another example, the accessory device may comprise a guidewire having proximal end portion and a distal end portion.

Alternatively or additionally to any of the examples above, in another example, the proximal portion of the guidewire may extend along a longitudinal axis and the distal portion of the guidewire may be configured to extend at an angle to the longitudinal axis.

Alternatively or additionally to any of the examples above, in another example, the angle may be in the range of 10 to 50°.

Alternatively or additionally to any of the examples above, in another example, the angle may be in the range of 15 to 35°.

Alternatively or additionally to any of the examples above, in another example, the guidewire may comprise a bent portion disposed between the proximal end portion and the distal end portion of the guidewire.

Alternatively or additionally to any of the examples above, in another example, the bent portion of the guidewire may be configured to deflect a portion of the catheter tube positioned distal to the bent portion.

Alternatively or additionally to any of the examples above, in another example, when the bent portion is positioned at a first longitudinal location within the catheter lumen, the thrombectomy catheter may have a first sweep coverage and when the bent portion is positioned at a second longitudinal location within the catheter lumen, the second location proximal to the first location, the thrombectomy catheter may have a second sweep coverage greater than the first sweep coverage.

Alternatively or additionally to any of the examples above, in another example, the thrombectomy catheter may further comprise a control handle releasably secured adjacent to a proximal end of the accessory device.

Alternatively or additionally to any of the examples above, in another example, the control handle may comprise a body portion, a slide portion, and a collet portion.

Alternatively or additionally to any of the examples above, in another example, the collet portion may be configured to be releasably secured to the accessory device.

Alternatively or additionally to any of the examples above, in another example, the control handle may be configured to rotate independent of the catheter body.

Alternatively or additionally to any of the examples above, in another example, the accessory device may be configured to rotate with rotation of the control handle.

In another example, a thrombectomy catheter may comprise a catheter tube extending from a catheter proximal portion to a catheter distal portion and including a catheter lumen extending between the catheter proximal portion and the catheter distal portion, a high pressure tube extending through the catheter lumen from the catheter proximal portion toward the catheter distal portion, the high pressure tube configured for communication with a fluid source near the catheter proximal portion, a fluid jet emanator in communication with the high pressure tube, the fluid jet emanator having at least one jet orifice for directing at least one fluid jet from said fluid jet emanator through the catheter lumen, an outflow orifice located along a catheter perimeter of the catheter distal portion, an entrainment inflow orifice positioned along the catheter distal portion, a guidewire slidably and rotatably disposed within the catheter lumen, the guidewire comprising a proximal portion, a distal portion, and a bent portion positioned between the proximal and distal portions, and a handle releasably secured to the guidewire adjacent to a distal end of the guidewire. The distal portion of the guidewire may extend at an angle relative to a longitudinal axis of the proximal portion of the guidewire.

Alternatively or additionally to any of the examples above, in another example, the angle may be in the range of 10 to 50°.

Alternatively or additionally to any of the examples above, in another example, the angle may be in the range of 15 to 35°.

Alternatively or additionally to any of the examples above, in another example, the bent portion of the guidewire may be configured to deflect a portion of the catheter tube positioned distal to the bent portion.

Alternatively or additionally to any of the examples above, in another example, when the bent portion is positioned at a first longitudinal location within the catheter lumen, the thrombectomy catheter may have a first sweep coverage and when the bent portion is positioned at a second longitudinal location within the catheter lumen, the second location proximal to the first location, the thrombectomy catheter may have a second sweep coverage greater than the first sweep coverage.

In another example, a thrombectomy catheter may comprise a catheter tube extending from a catheter proximal portion to a catheter distal portion and including a catheter lumen extending between the catheter proximal portion and the catheter distal portion, a high pressure tube extending through the catheter lumen from the catheter proximal portion toward the catheter distal portion, the high pressure tube configured for communication with a fluid source near the catheter proximal portion, a fluid jet emanator in communication with the high pressure tube, the fluid jet emanator having at least one jet orifice for directing at least one fluid jet from said fluid jet emanator through the catheter lumen, an outflow orifice located along a catheter perimeter of the catheter distal portion, an entrainment inflow orifice positioned along the catheter distal portion, a guidewire slidably and rotatably disposed within the catheter lumen, the guidewire comprising a proximal portion, a distal portion, and a bent portion positioned between the proximal and distal portions, and a handle releasably secured to the guidewire adjacent to a distal end of the guidewire. The distal portion of the guidewire may extend at an angle relative to a longitudinal axis of the proximal portion of the guidewire and the guidewire may have a stiffness that is less than a stiffness of the catheter proximal portion and greater than a stiffness of the catheter distal portion.

Alternatively or additionally to any of the examples above, in another example, the bent portion may have a radius of curvature in the range of 1 to 2 millimeters.

In another example, a thrombectomy catheter may comprise a catheter tube extending from a catheter proximal portion to a catheter distal portion and including a catheter lumen extending between the catheter proximal portion and the catheter distal portion, a high pressure tube extending through the catheter lumen from the catheter proximal portion toward the catheter distal portion, the high pressure tube configured for communication with a fluid source near the catheter proximal portion, a fluid jet emanator in communication with the high pressure tube, the fluid jet emanator having at least one jet orifice for directing at least one fluid jet from said fluid jet emanator through the catheter lumen, an outflow orifice located along a catheter perimeter of the catheter distal portion, an entrainment inflow orifice positioned along the catheter distal portion, and an accessory device disposed within the catheter lumen.

Alternatively or additionally to any of the examples above, in another example, the accessory device may comprise a guidewire having a proximal end region and a distal end region and an expandable cage affixed adjacent to the distal end region of the guidewire.

Alternatively or additionally to any of the examples above, in another example, the expandable cage may comprise a plurality of struts extending from a proximal end of the cage to a distal end of the cage.

Alternatively or additionally to any of the examples above, in another example, each strut of the plurality of struts may be formed from two or more wires.

Alternatively or additionally to any of the examples above, in another example, a proximal end of each strut of the plurality of struts may be coupled to the guidewire.

Alternatively or additionally to any of the examples above, in another example, the expandable cage may be configured to move between a collapsed configuration and an expanded configuration.

Alternatively or additionally to any of the examples above, in another example, in the expanded configuration, the struts may be configured to curve away from a longitudinal axis of the guidewire along a length of the struts such that a cross-sectional diameter of the cage in the expanded configuration is larger than a cross-sectional diameter of the cage in the collapsed configuration.

Alternatively or additionally to any of the examples above, in another example, in the expanded configuration, each strut of the plurality of struts may have a generally helically shape such that a distal end of each strut is circumferentially offset from a proximal end of said strut.

Alternatively or additionally to any of the examples above, in another example, the thrombectomy catheter may further comprise a control handle releasably coupled adjacent to a proximal end region of the guidewire.

Alternatively or additionally to any of the examples above, in another example, the control handle may be configured to move longitudinally and/or rotationally independent of the catheter tube.

Alternatively or additionally to any of the examples above, in another example, the accessory device may be configured to move with movement of the control handle Alternatively or additionally to any of the examples above, in another example, the guidewire may further comprise a bent portion disposed between the proximal end region and the distal end region and the proximal end region of the guidewire wire may extend along a longitudinal axis and the distal end region of the core wire may extend from the bent portion at an angle to the proximal end region.

Alternatively or additionally to any of the examples above, in another example, the guidewire may be configured to deflect the catheter distal portion from a longitudinal axis of the catheter proximal portion.

Alternatively or additionally to any of the examples above, in another example, an amount of deflection of the catheter distal portion varies with a longitudinal location of the bent portion of the guidewire.

Alternatively or additionally to any of the examples above, in another example, the plurality of struts may comprise in the range of two to twenty struts.

In another example, a thrombectomy catheter may comprise a catheter tube extending from a catheter proximal portion to a catheter distal portion and including a catheter lumen extending between the catheter proximal portion and the catheter distal portion, a high pressure tube extending through the catheter lumen from the catheter proximal portion toward the catheter distal portion, the high pressure tube configured for communication with a fluid source near the catheter proximal portion, a fluid jet emanator in communication with the high pressure tube, the fluid jet emanator having at least one jet orifice for directing at least one fluid jet from said fluid jet emanator through the catheter lumen, an outflow orifice located along a catheter perimeter of the catheter distal portion, an entrainment inflow orifice positioned along the catheter distal portion and an accessory device disposed within the catheter lumen.

Alternatively or additionally to any of the examples above, in another example, the accessory device may comprise a guidewire having a proximal end region and a distal end region and an expandable cage affixed adjacent to the distal end region of the guidewire.

Alternatively or additionally to any of the examples above, in another example, the expandable cage may comprise a plurality of struts extending from a proximal end of the cage to a distal end of the cage.

Alternatively or additionally to any of the examples above, in another example, each strut of the plurality of struts may be formed from two or more wires.

Alternatively or additionally to any of the examples above, in another example, a proximal end of each strut of the plurality of struts may be coupled to the guidewire.

Alternatively or additionally to any of the examples above, in another example, the expandable cage may be configured to move between a collapsed configuration and an expanded configuration.

Alternatively or additionally to any of the examples above, in another example, in the expanded configuration, the struts may be configured to curve away from a longitudinal axis of the guidewire along a length of the struts such that a cross-sectional diameter of the cage in the expanded configuration is larger than a cross-sectional diameter of the cage in the collapsed configuration.

Alternatively or additionally to any of the examples above, in another example, in the expanded configuration, each strut of the plurality of struts may have a generally helically shape such that a distal end of each strut is circumferentially offset from a proximal end of said strut.

Alternatively or additionally to any of the examples above, in another example, the thrombectomy catheter may further comprise a control handle releasably coupled adjacent to a proximal end region of the guidewire.

Alternatively or additionally to any of the examples above, in another example, the guidewire may further comprise a bent portion disposed between the proximal end region and the distal end region and the proximal end region of the guidewire wire may extend along a longitudinal axis and the distal end region of the core wire may extend from the bent portion at an angle to the proximal end region.

Alternatively or additionally to any of the examples above, in another example, the guidewire may be configured to deflect the catheter distal portion from a longitudinal axis of the catheter proximal portion.

Alternatively or additionally to any of the examples above, in another example, an amount of deflection of the catheter distal portion varies with a longitudinal location of the bent portion of the guidewire.

In another example a thrombectomy catheter may comprise a catheter tube extending from a catheter proximal portion to a catheter distal portion and including a catheter lumen extending between the catheter proximal portion and the catheter distal portion, a high pressure tube extending through the catheter lumen from the catheter proximal portion toward the catheter distal portion, the high pressure tube configured for communication with a fluid source near the catheter proximal portion, a fluid jet emanator in communication with the high pressure tube, the fluid jet emanator having at least one jet orifice for directing at least one fluid jet from said fluid jet emanator through the catheter lumen, an outflow orifice located along a catheter perimeter of the catheter distal portion, an entrainment inflow orifice positioned along the catheter distal portion, an accessory device disposed within the catheter lumen. The accessory device may comprise a guidewire having a proximal end region and a distal end region, an expandable cage comprising a plurality of struts affixed adjacent to the distal end region of the guidewire, and a control handle releasably coupled adjacent to a proximal end region of the guidewire.

Alternatively or additionally to any of the examples above, in another example, the plurality of struts may comprise in the range of two to twenty struts.

Alternatively or additionally to any of the examples above, in another example, each strut of the plurality of struts may be formed from two or more wires.

Alternatively or additionally to any of the examples above, in another example, the expandable cage may be configured to move between a collapsed configuration and an expanded configuration.

Alternatively or additionally to any of the examples above, in another example, in the expanded configuration, the struts may be configured to curve away from a longitudinal axis of the guidewire along a length of the struts such that a cross-sectional diameter of the cage in the expanded configuration is larger than a cross-sectional diameter of the cage in the collapsed configuration.

Alternatively or additionally to any of the examples above, in another example, in the expanded configuration, each strut of the plurality of struts may have a generally helically shape such that a distal end of each strut is circumferentially offset from a proximal end of said strut.

Alternatively or additionally to any of the examples above, in another example, the guidewire further may comprise a bent portion disposed between the proximal end region and the distal end region and the proximal end region of the guidewire wire may extend along a longitudinal axis and the distal end region of the core wire may extend from the bent portion at an angle to the proximal end region.

In another example, a thrombectomy catheter may comprise a catheter tube extending from a catheter proximal portion to a catheter distal portion and including a catheter lumen extending between the catheter proximal portion and the catheter distal portion, a high pressure tube extending through the catheter lumen from the catheter proximal portion toward the catheter distal portion, the high pressure tube configured for communication with a fluid source near the catheter proximal portion, a fluid jet emanator in communication with the high pressure tube, the fluid jet emanator having at least one jet orifice for directing at least one fluid jet from said fluid jet emanator through the catheter lumen, an outflow orifice located along a catheter perimeter of the catheter distal portion, an entrainment inflow orifice positioned along the catheter distal portion, and an accessory device disposed within the catheter lumen. The accessory device may comprise a guidewire having a proximal end region and a distal end region, an expandable cage configured to move between a collapsed configuration and an expanded configuration, the expandable cage comprising a plurality of struts affixed adjacent to the distal end region of the guidewire, and a control handle releasably secured adjacent to a proximal end of the guidewire, the control handle and the guidewire configured to move longitudinally and rotationally independent of the catheter tube. In the expanded configuration, each strut of to the plurality of struts may have a generally helically shape such that a distal end of each strut is circumferentially offset from a proximal end of said strut.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
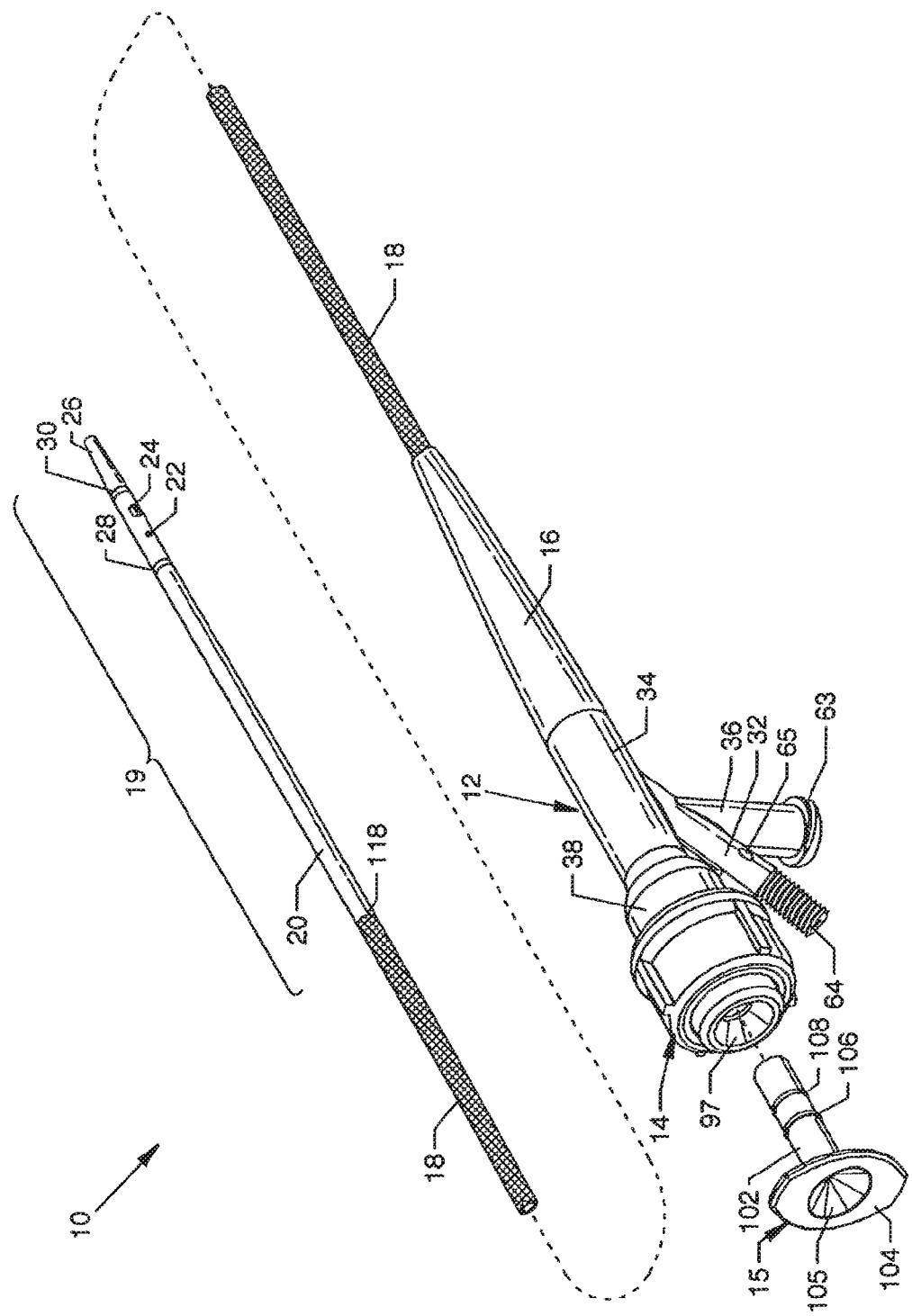
FIG. 1 is an isometric view of a cross stream mechanical thrombectomy catheter with a backloading manifold.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

All numeric values are herein assumed to be modified by the term "about", whether or not explicitly indicated. The term "about" generally refers to a range of numbers that one of skill in the art would consider equivalent to the recited value (e.g., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Thrombectomy catheters and systems may be used to remove thrombus, plaques, lesions, clots, etc. from veins or arteries. These devices may be effective to remove acute thrombus but may be less effective on older or more organized thrombus, or areas of large clot burden such as that seen in deep vein thrombosis (DVT). It may be desirable to provide a thrombectomy catheter with an accessory device to be used in combination with the thrombectomy catheter.

FIG. 1 is an isometric view of an enhanced cross stream mechanical thrombectomy catheter with a backloading manifold 10. Externally visible major components of an embodiment of the present disclosure may include a centrally located backloading manifold 12, a flexible and tapered strain relief 16 connected to and extending from the backloading manifold 12, a catheter tube extending from a proximal portion to a distal portion and composed of a braided catheter tube 18 connected to the backloading manifold 12 and extending through the tapered and flexible strain relief 16 and a smooth catheter tube assembly 19 having a smooth catheter tube 20 connected to and extending distally from the braided catheter tube 18. The components of the smooth catheter tube assembly 19 are depicted fully in FIGS. 2 and 3. In some cases, the braided catheter tube may be formed of a flexible or semi-flexible material, such as but not limited to polyimide or other such suitable composition. It is contemplated that the smooth catheter tube 20 may be formed of a plastic composition, although this is not required. In some cases, the catheter tube 18 is formed as a braided construction for strength, as shown, but it can be effectively formed in other ways: for example, by using reinforcing components such as fibers, wound strands, rings, wraps, or combinations thereof. Also shown is the junction 118 between the smooth catheter tube 20 and the braided catheter tube 18, such junction being suitably effected to provide for a smooth and continuous coupling of the smooth catheter tube 20 and the braided catheter tube 18.

An outflow orifice 22 and an entrainment inflow orifice 24 may be located in longitudinal alignment along an imaginary line at the distal portion of the smooth catheter tube 20 near a flexible tapered tip 26 located distally at the end of the smooth catheter tube 20. For illustration purposes, the outflow orifice 22 and the inflow orifice 24, which extend through the smooth catheter tube 20, are shown on the side of the smooth catheter tube 20, but can be located along any imaginary line extending longitudinally along a distal surface of the smooth catheter tube 20, such as is shown in FIGS. 3, 7, 10, and 11. In some embodiments, the thrombectomy catheter 10 may further include a radiopaque marker band 28 located on the smooth catheter tube 20 in close proximity to and proximal to the outflow orifice 22, a radiopaque marker band 30 located on the smooth catheter tube 20 in close proximity to and distal to the inflow orifice 24.

The backloading manifold 12 may further include a central body 34 having a proximally located cavity body 38. The central body 34 may be coupled to a proximal end of the strain relief 16. A hemostatic nut 14 may be threadingly secured to the backloading manifold 12. The hemostatic nut 14 may include a beveled surface entrance configured to receive an introducer 15. The introducer 15 may include a centrally located shaft 102 with a beveled surface entrance 105, an actuating handle 104, and rings 106 and 108 about the shaft 102.

Other externally visible major components may include, a high pressure connection branch 32 extending from the central body 34 of the backloading manifold 12, an exhaust branch 36 extending from the junction of the central body 34 of the backloading manifold 12 and the high pressure connection branch 32, and a high pressure connector 64 engaging with and extending from the high pressure connection branch 32 of the backloading manifold 12. An orifice 65 located in the high pressure connection branch 32 may allow for the introduction of an adhesive 61 (see, for example, FIG. 5) to secure the high pressure connector 64 in the high pressure connection branch 32. The exhaust branch 36 may have a threaded surface 63 at its end for attaching to suction apparatus.

Figure 2:
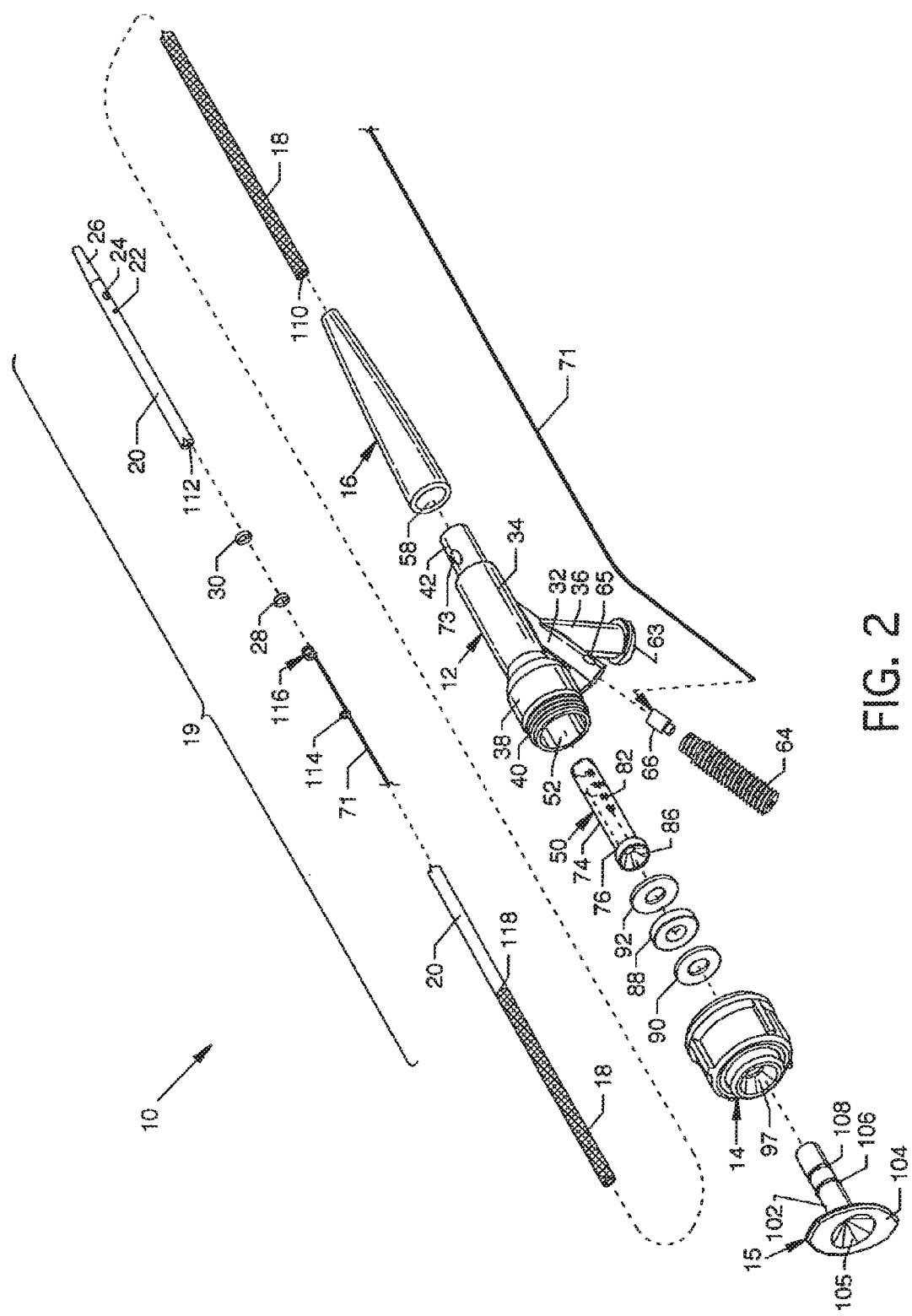
FIG. 2 is an isometric exploded view of the cross stream mechanical thrombectomy catheter with a backloading manifold.
Figure 3:
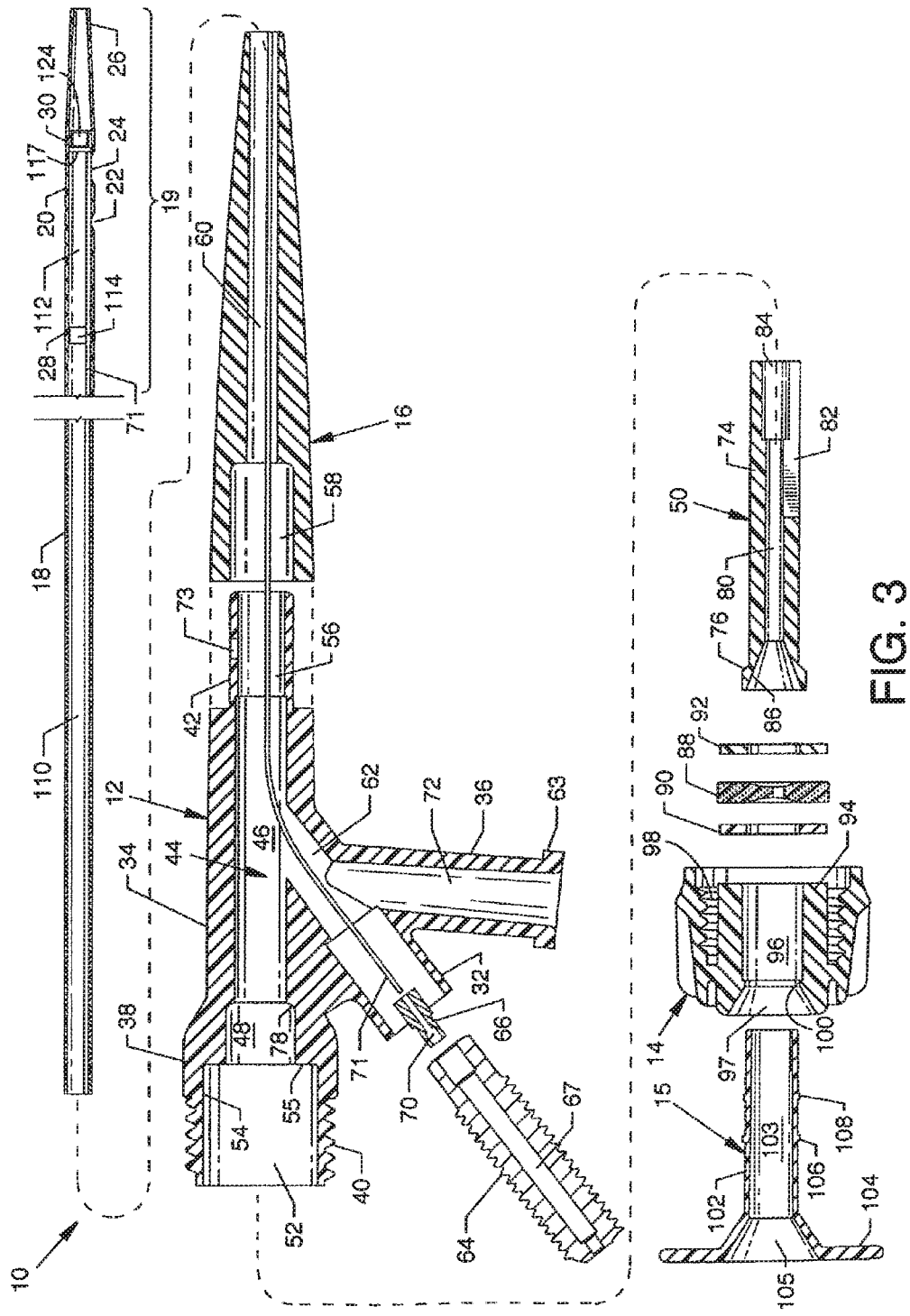
FIG. 3 is an exploded cross section side view of the components of the cross stream mechanical thrombectomy catheter with a backloading manifold.

FIG. 2 is an isometric exploded view of the enhanced cross stream mechanical thrombectomy catheter with backloading manifold 10, and FIG. 3 is an exploded cross section side view of the components of the enhanced cross stream mechanical thrombectomy catheter with a backloading manifold 10.

Figure 5:
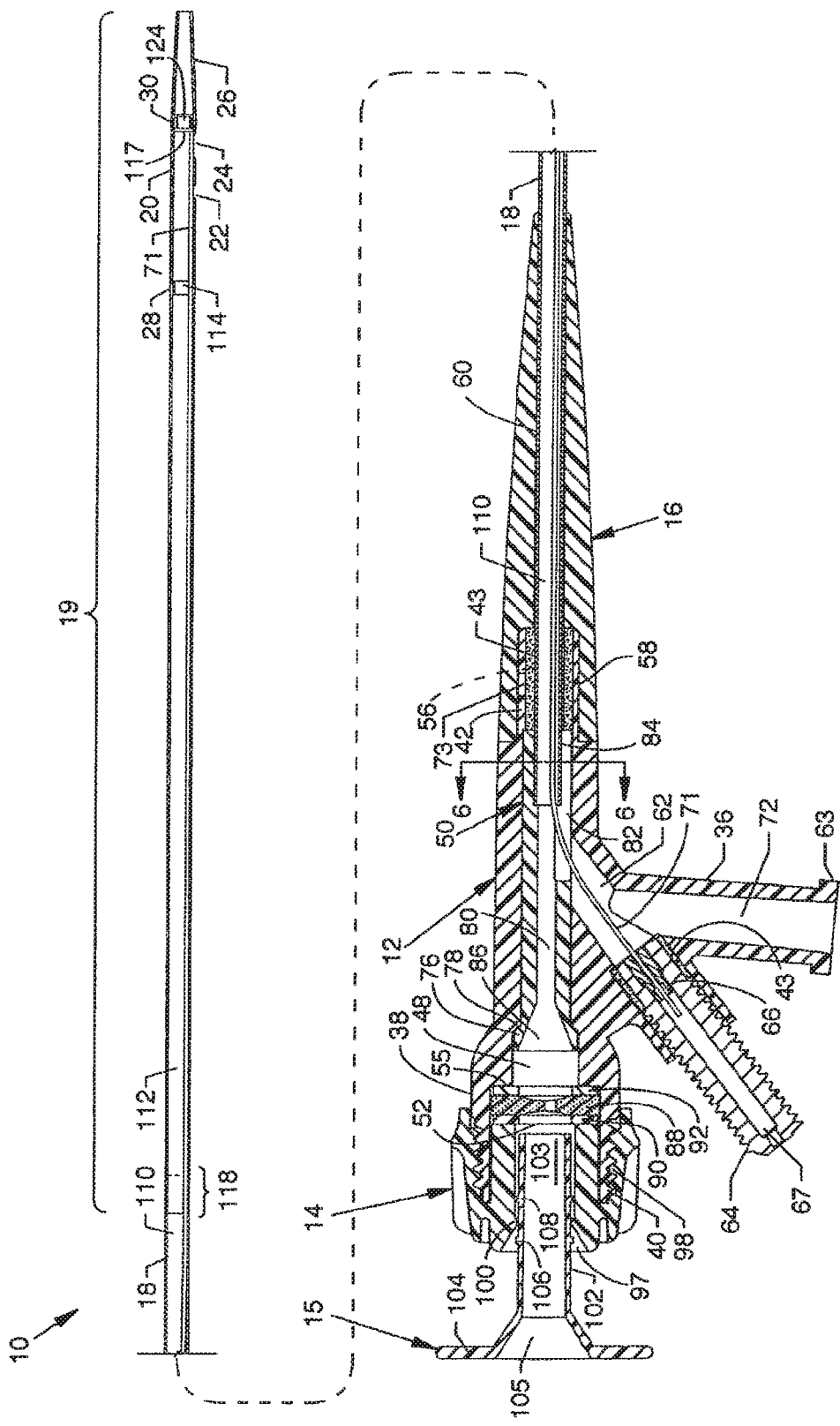
FIG. 5 is a cross section view of the assembled elements of FIG. 3.

As described herein, the backloading manifold 12 may include the central body 34 which may be tubular and have on one end a proximally located cavity body 38 including an externally located threaded surface 40 and on the other end a distally located tubular manifold extension 42, including an orifice 73 which may be utilized to introduce adhesive 43 (as shown in FIG. 5) to secure the proximal end of the braided catheter tube 18 to the distal manifold cavity 56. A multi-radius insert cavity 44 is continuously co-located within the central body 34 and a portion of the adjacent cavity body 38. The multi-radius insert cavity 44 is comprised of an elongated distal insert cavity portion 46 located coaxially within the central body 34 adjacent to and connecting to a proximal insert cavity portion 48 located coaxial to the cavity body 38 in continuous fashion. The insert cavity 44 accommodates an insert 50. The entire insert 50 is accommodated by the insert cavity 44 where the distal insert cavity portion 46 and the proximal insert cavity portion 48 fittingly accommodate separate geometric configurations of the insert 50.

A proximal manifold cavity 52 is located coaxially within the cavity body 38 and is continuous with and proximal to the proximal insert cavity portion 48 and an annular cavity wall 54 and an annular and planar surface 55 located between the annular cavity wall 54 and the proximal insert cavity portion 48. The manifold extension 42 extending distally from the distal end of the backloading manifold 12 includes an inwardly located distal manifold cavity 56 for passage of the proximal end of the braided catheter tube 18. The exterior of the manifold extension 42 accommodates the strain relief 16. The strain relief 16 is of flexible construction and includes a proximally located strain relief mounting cavity 58 connected to a passageway 60 both of which extend along the longitudinal axis of the strain relief 16. The strain relief mounting cavity 58 accommodates the manifold extension 42, which can be appropriately secured therein, such as by adhesive or mechanical interference.

The high pressure connection branch 32 includes a high pressure connection branch passageway 62 intersecting and communicating with the distal insert cavity portion 46 of the insert cavity 44, as well as offering accommodation of the threaded high pressure connector 64. The threaded high pressure connector 64 may be configured to be operatively coupled to a fluid source positioned near the proximal portion of the catheter 18, 20 to provide communication between the fluid source and the high pressure tube 71. In some cases, the fluid source may be directly coupled to the high pressure connector 64 and in other cases the fluid source may be indirectly coupled to the high pressure connector 64. A ferrule 66 having a central bore 70 is accommodated by the lumen 67 of the high pressure connector 64. One end of a high pressure tube 71 is accommodated by and sealingly secured to the central bore 70 of the ferrule 66, such as by a weldment or mechanical interference. An exhaust branch passageway 72 central to the exhaust branch 36 communicates with the high pressure connection branch passageway 62 and with the distal insert cavity portion 46 of the insert cavity 44. The exhaust branch 36 has a threaded surface 63 at its end for attaching to a suction apparatus. As also shown in the isometric view of FIG. 4, the insert 50 includes a tubular main body 74 having a proximally located shoulder 76 which can be tapered or of other suitable geometric configuration. The shoulder 76 engages an annular transition stop surface 78 (FIG. 3) between the proximal insert cavity portion 48 and the distal insert cavity portion 46. One end of a central passageway 80 truncatingly intersects an elongated slot 82; and such central passageway also intersects a bore 84 which is also truncated by intersecting the elongated slot 82, e.g., the central passageway 80 adjoins bore 84 and each is truncated by intersection with the elongated slot 82. The elongated slot 82 extends through the main body 74 to intersect and align to a portion of the longitudinal axis of the insert 50. The elongated slot 82 accommodates passage of the high pressure tube 71, as shown in FIG. 5. The central passageway 80 has a proximally located beveled surface entrance 86 resembling a cone. The beveled surface entrance 86 is utilized for guidance and alignment for backloading of a guidewire through the backloading manifold 12, as described herein.

Beneficial to an embodiment of the present disclosure is the use of a self-sealing hemostatic valve 88, flanking washers 90 and 92, and an introducer 15 which are related to a patent application entitled "Thrombectomy Catheter Device Having a Self-Sealing Hemostatic Valve," U.S. Pat. No. 7,226,433, which is herein incorporated by reference. The self-sealing hemostatic valve 88, which is slightly oversized with respect to the proximal manifold cavity 52, and the washers 90 and 92 are aligned in and housed in the proximal manifold cavity 52 at one end of the backloading manifold 12. The hemostatic nut 14 includes a centrally located cylindrical boss 94, a central passageway 96 having a beveled surface entrance 97 extending through and in part forming the cylindrical boss 94, and internal threads 98. The internal threads 98 of the hemostatic nut 14 can be made to engage the threaded surface 40 of the backloading manifold 12, whereby the cylindrical boss 94 is brought to bear against the washer 90 to resultantly bring pressure to bear as required against the self-sealing hemostatic valve 88 and washer 92. The washers 90 and 92 and the self-sealing hemostatic valve 88 are captured in the proximal manifold cavity 52 by threaded engagement of the hemostatic nut 14 to the cavity body 38 of the backloading manifold 12. Also included in the hemostatic nut 14 is an annular lip 100 which can be utilized for snap engagement of particular styles or types of introducers, as required, such as introducer 15 provided to aid in accommodation of a guidewire in either direction and to provide for venting for the interior of the backloading manifold 12. The introducer 15 includes a centrally located shaft 102 with a central passageway 103 having a beveled surface entrance 105, an actuating handle 104, and rings 106 and 108 about the shaft 102.

Also shown in FIG. 3 is a catheter lumen 110 central to the braided catheter tube 18 which joiningly connects to and communicates with a lumen 112 central to the smooth catheter tube 20 to form a lumen extending between the catheter proximal portion and the catheter distal portion or, in other words, the proximal portion and the distal portion of the catheter tube. The high pressure tube 71 may extend through the lumen 1110 of the braided catheter tube 18 and the lumen 112 of the smooth catheter tube 20. A circular support ring 114 is suitably attached to the high pressure tube 71, such as by a weldment, and is located within the smooth catheter tube 20 in supporting alignment with the radiopaque marker band 28. A fluid jet emanator 116 including terminated loop 117 at and in fluid communication with the distal end of the high pressure tube 71 and a circular support ring 124 is located distal of the inflow orifice 24 within the distal end of the smooth catheter tube 20 in alignment with the radiopaque marker band 30, as described in detail with respect to FIG. 10. The circular support rings 114 and 124 together with the respective associated radiopaque marker bands 28 and 30 constitute means for retaining the high pressure tube 71 in alignment with the catheter tube composed of braided catheter tube 18 and the smooth catheter tube 20.

Figure 4:
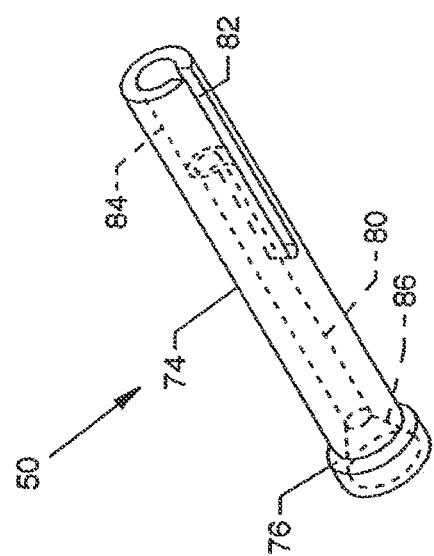
FIG. 4 is an isometric view of the insert showing an elongated slot extending through the main body.

FIG. 4 is an isometric view of the insert 50 showing the elongated slot 82 extending through the main body 74 in intersection with the central passageway 80 and the bore 84. The elongated slot 82 is beneficial for accommodation of the high pressure tube 71, as well as for communication between the combined lumens 110 and 112 of the braided catheter tube 18 and the smooth catheter tube 20, respectively, and the high pressure connection branch passageway 62 and the exhaust branch passageway 72, as shown in FIG. 5.

FIG. 5 is a cross section view of the assembled elements of FIG. 3. Particularly shown is the relationship of the high pressure tube 71, the insert 50, the lumen 110 of the braided catheter tube 18, and the proximal end of the braided catheter tube 18. The proximal portion of the high pressure tube 71 extends distally from the ferrule 66 through the high pressure connection branch passageway 62, through the elongated slot 82 of the insert 50 while traversing the distal portion of the central passageway 80 en route to and into the lumen 110 of the braided catheter tube 18, and thence along the lumen 110 and into the lumen 112 of the smooth catheter tube 20 to terminate as part of the fluid jet emanator 116 shown adjacent to the flexible tapered tip 26 at the distal end of the smooth catheter tube 20. In addition to providing a passage for the high pressure tube 71, the elongated slot 82 allows communication between the lumen 110 of the braided catheter tube 18 and the lumen 112 of the smooth catheter tube 20, collectively, and the high pressure connection branch passageway 62 and the exhaust branch passageway 72 for evacuation of effluence therefrom. Also shown is the junction 118 between the smooth catheter tube 20 and the braided catheter tube 18, such junction being suitably effected to provide for a smooth and continuous coupling of the smooth catheter tube 20 and the braided catheter tube 18.

Figure 6:
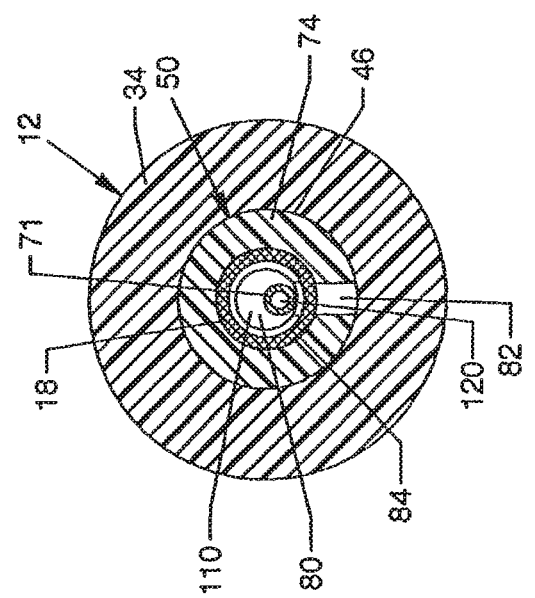
FIG. 6 is a cross section view of the cross stream mechanical thrombectomy catheter with a backloading manifold along line 6-6 of FIG. 5.

FIG. 6 is a cross section view of the enhanced cross stream mechanical thrombectomy catheter with backloading manifold 10 along line 6-6 of FIG. 5. Shown in particular is the elongated slot 82 through which the high pressure tube 71 passes (passage of high pressure tube 71 not shown) and through which communication takes place between the lumen 110 of the braided catheter tube 18 and the high pressure connection branch passageway 62 and the exhaust branch passageway 72. Also shown is a lumen 120 central to the high pressure tube 71.

Figure 7:
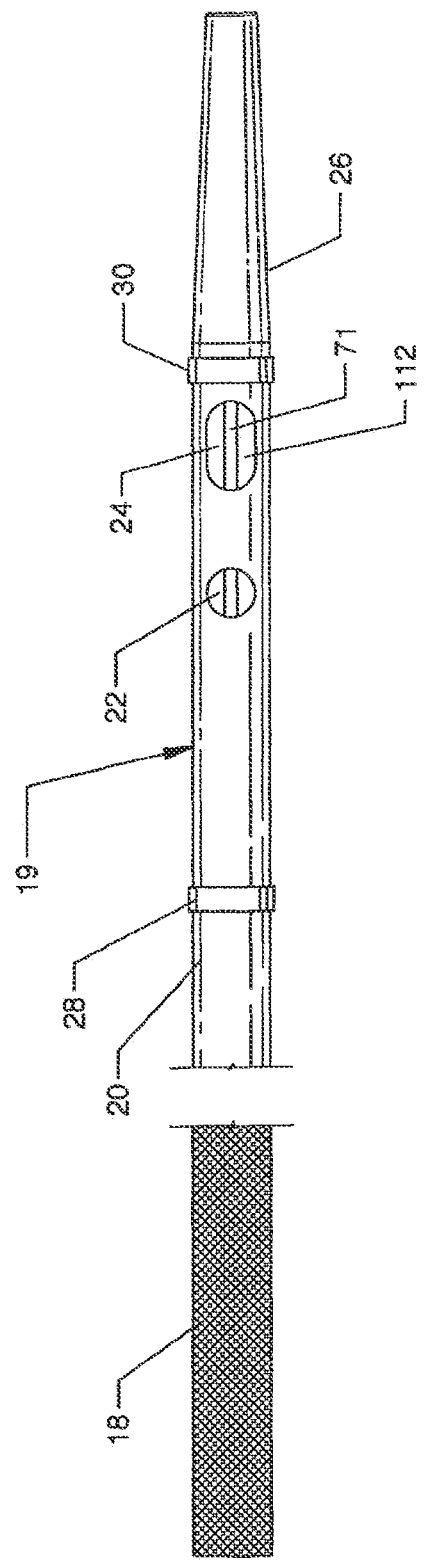
FIG. 7 is a bottom view of the distal end of the cross stream mechanical thrombectomy catheter with a backloading manifold showing the smooth catheter tube, the outflow orifice, and the inflow orifice, as well as the high pressure tube visible through the outflow orifice and the inflow orifice.

FIG. 7 is a bottom view of the distal end of the enhanced cross stream mechanical thrombectomy catheter with backloading manifold 10 showing the smooth catheter tube 20 and the outflow orifice 22 and the inflow orifice 24, as well as the high pressure tube 71 visible through the outflow orifice 22 and the inflow orifice 24.

Figure 8:
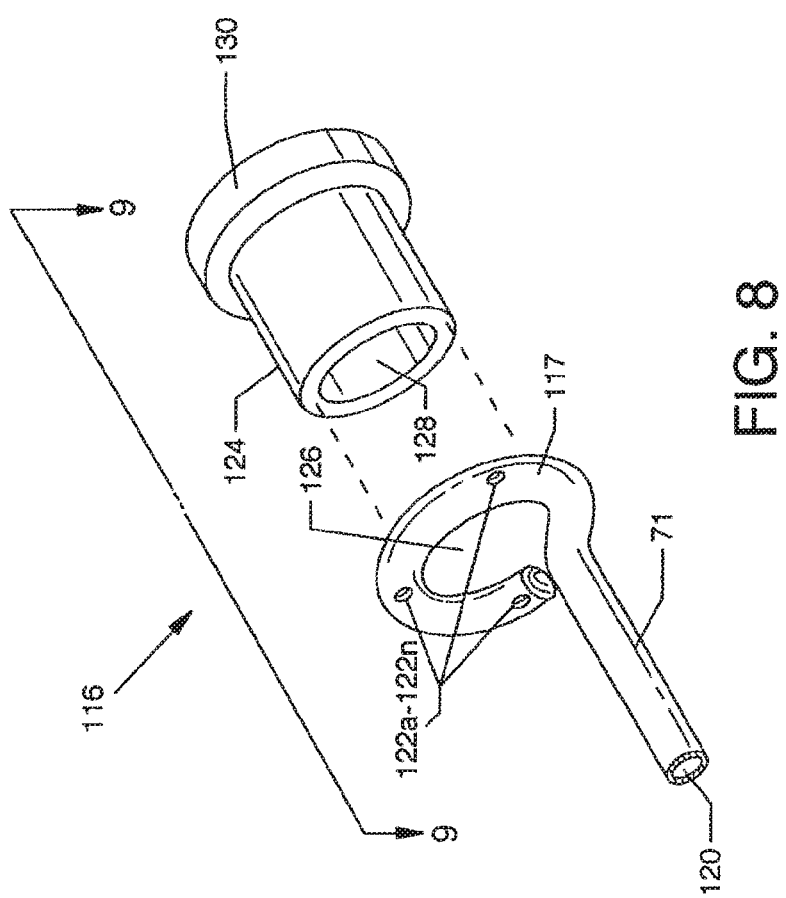
FIG. 8 is an exploded isometric view of the fluid jet emanator.
Figure 9:
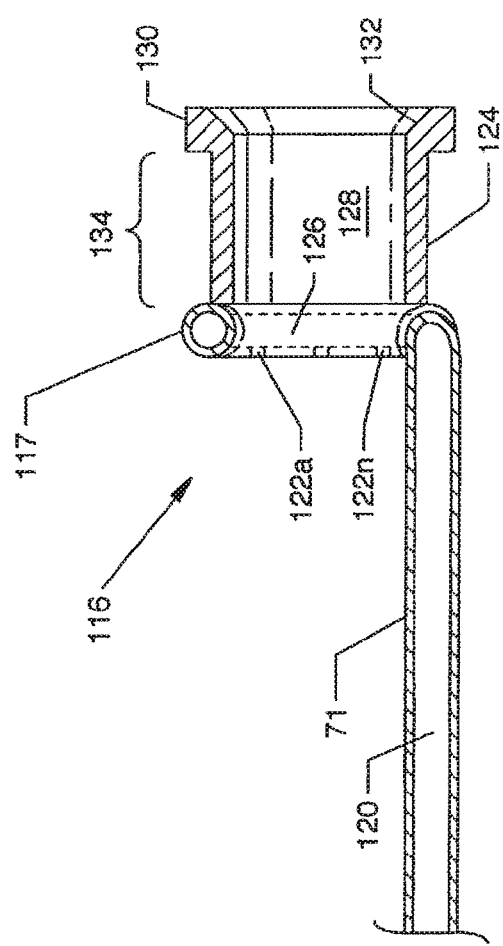
FIG. 9 is an assembled side view in cross section along line 9-9 of FIG. 8 of the fluid jet emanator.
Figure 10:
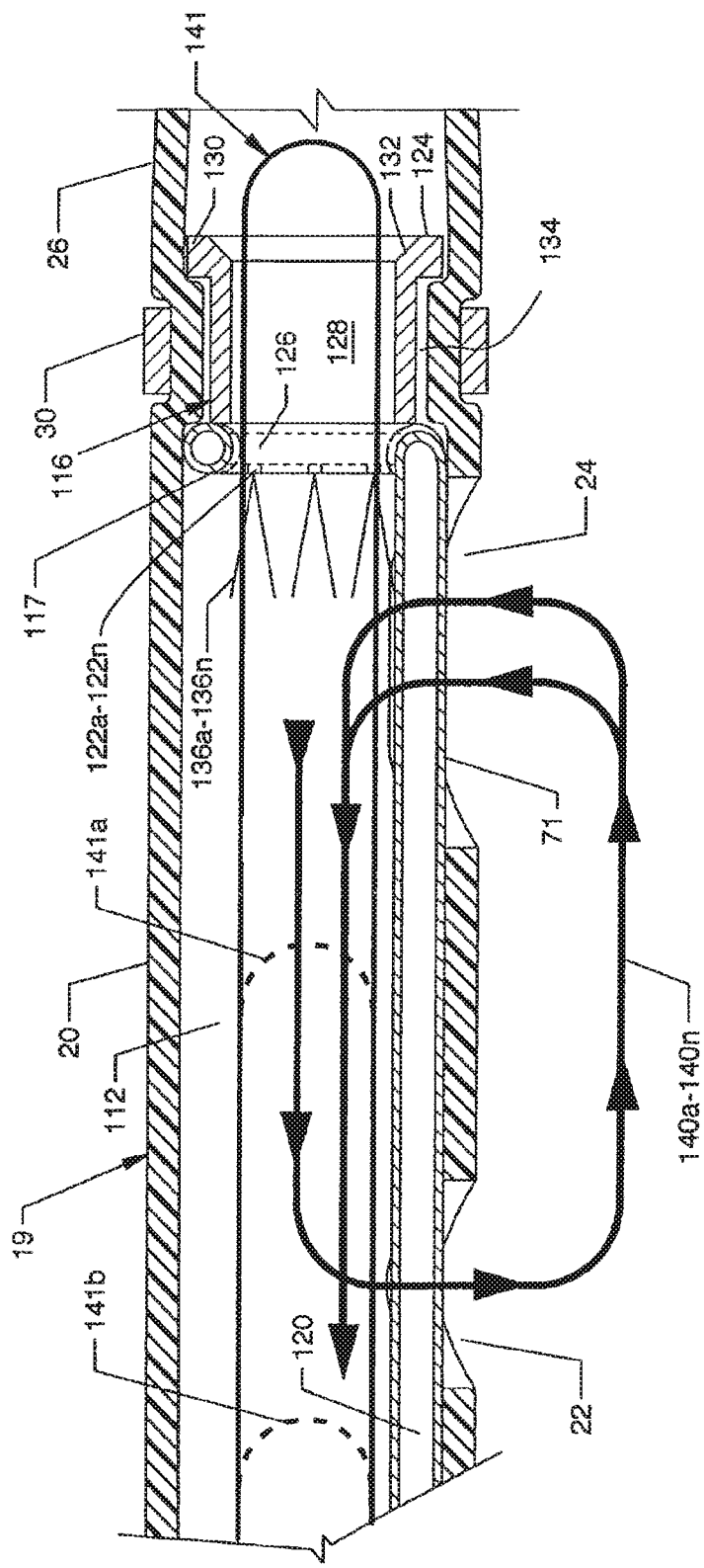
FIG. 10 is a side view in cross section illustrating the elements of FIG. 9 secured in the distal portion of the smooth catheter tube by a radiopaque marker band, as well as showing the cross stream flow.

FIG. 8 is an exploded isometric view and FIG. 9 is an assembled side view in cross section along line 9-9 of FIG. 8 of the fluid jet emanator 116. The fluid jet emanator 116 includes a terminated loop 117 at the distal end of the high pressure tube 71 and includes the support ring 124. The terminated loop 117 includes a plurality of proximally directed jet orifices 122a-122n (collectively, 122). The support ring 124 suitably secures to the distal surface of the terminated loop 117 such as by a weldment. A center void 126 of the terminated loop 117 allows for passage of a guidewire or other suitable devices. The support ring 124, a tubular device, includes a central passageway 128 corresponding in use to that of the center void 126 of the terminated loop 117 for passage of a guidewire or other suitable devices. A distally located annular shoulder 130 on the support ring 124 allows for the inclusion of a beveled annular surface 132 juxtaposing the central passageway 128 to aid in the guided accommodation of a guidewire or other suitable device at the distal portion of the central passageway 128. A wide annular groove 134 is formed between the annular shoulder 130 and the distally facing surface of the terminated loop 117 and the smaller radiused body of the support ring 124. The wide annular groove 134 is utilized to secure the fluid jet emanator 116 at a suitable location in the distal portion of the smooth catheter tube 20, as shown in FIG. 10.

The mode of operation of the enhanced cross stream mechanical thrombectomy catheter with backloading manifold 10 is explained with reference to FIGS. 10, 11, and 12. FIG. 10 illustrates the elements of FIG. 9 secured in the distal portion of the smooth catheter tube 20 by the radiopaque marker band 30 which forces an annular portion of the smooth catheter tube 20 into the wide annular groove 134 formed by the support ring 124 and the terminated loop 117 of the fluid jet emanator 116. High velocity fluid jets 136a-136n (collectively, 136) are shown emanating proximally from the plurality of jet orifices 122a-122n (collectively, 122) into the lumen 112 of the smooth catheter tube 20 for subsequent creation of and culminating in cross stream jets 140a-140n (collectively, 140), as depicted by heavy lines, which flow from the outflow orifice 22 and return through the inflow orifice 24 for ablative action with thrombus material and for maceration of foreign material in concert with the high velocity fluid jets 136a-136n and/or for exhausting proximally with the flow within the distal portion of the smooth catheter tube 20. A guidewire 141 is also shown in see-through depiction, including alternate guidewire end positions 141a and 141b designated by dashed lines, where the guidewire 141 extends along the lumen 112 of the smooth catheter tube 20, through the center void 126 of the terminated loop 117, and through the central passageway 128 of the support ring 124 into the proximal portion of the flexible tapered tip 26. Guidewire 141 can be advanced beyond the flexible tapered tip 26 of the smooth catheter tube 20 such as during positioning of the catheter within the blood vessel or other body cavity, and then withdrawn to alternate guidewire end positions 141a and 141b, or other positions within the smooth catheter tube 20, or withdrawn completely from the smooth catheter tube 20. An advantage of an embodiment of the present disclosure is that the guidewire 141 can be introduced by a front loading approach or by a backloading approach and, therefore, can be removed and reintroduced or can be replaced by a different guidewire.

Figure 11:
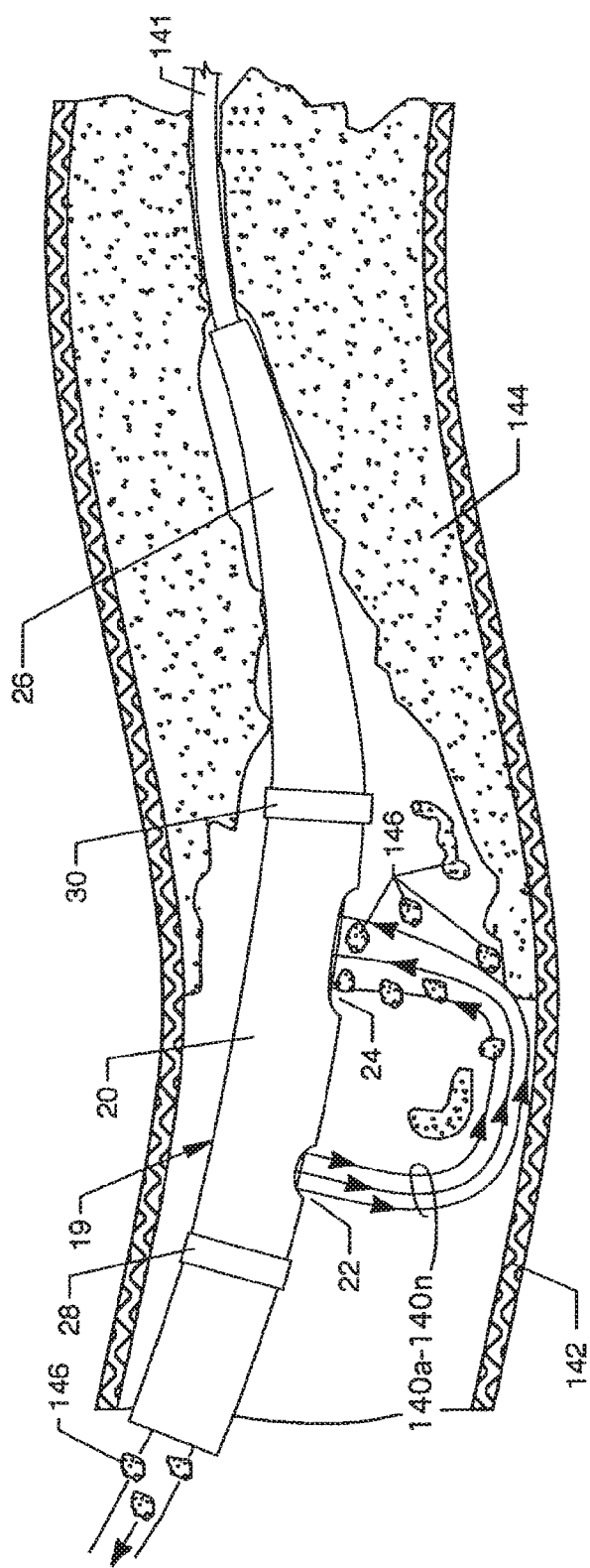
FIG. 11 is a side view of the distal region of the cross stream mechanical thrombectomy catheter with a backloading manifold showing the distal end of a smooth catheter tube assembly positioned in a blood vessel (shown in cross section) at a site of a thrombotic deposit or lesion.

FIG. 11 is a side view of the distal region of the enhanced cross stream mechanical thrombectomy catheter with a backloading manifold 10 showing in particular the distal end of the smooth catheter tube assembly 19 positioned in a blood vessel 142 (shown in cross section) at a site of a thrombotic deposit or lesion 144. While FIG. 11 depicts the smooth catheter tube assembly 19 as being in a blood vessel in particular, it is to be understood that it is not limited to use in a blood vessel but has utility with respect to any body cavity in general. High velocity fluid jets 136a-136n (shown in FIG. 10) of saline or other suitable solution are emanated or emitted in a proximal direction from the fluid jet emanator 116 into the smooth catheter tube 20 and pass through the outflow orifice 22 creating cross stream jets 140a-140n directed toward the wall of the blood vessel 142 having thrombotic deposits or lesions 144 and thence are influenced by the low pressure at the inflow orifice 24 to cause the cross stream jets 140a-140n to be directed distally substantially parallel to the central axis of the blood vessel 142 to impinge and break up thrombotic deposits or lesions 144 and to, by entrainment, urge and carry along the dislodged and ablated thrombotic particulates 146 of the thrombotic deposits or lesions 144 through the inflow orifice 24, a relatively low pressure region, and into the lumen 112, which functions as a recycling maceration lumen or chamber and also as an exhaust lumen. The entrainment through the inflow orifice 24 is based on entrainment by the high velocity fluid jets 136a-136n. The outflow is driven by internal pressure which is created by the high velocity fluid jets 136a-136n and the fluid entrained through the inflow orifice 24. The enhanced clot removal is enabled because of the recirculation pattern established between inflow orifice 24 and the outflow orifice 22, which creates a flow field that maximizes drag force on wall-adhered thrombus, and because of impingement of the cross stream jets 140a-140n. The cross stream jets 140a-140n, whilst being forcefully directed outwardly and toward the wall of the blood vessel 142, by opposite reaction urge the distal portion of the smooth catheter tube 20 in the direction opposite the outward flow direction and away from the impingement area of the cross stream jets 140a-140n with the immediate thrombotic deposit or lesion 144 and/or the wall of the blood vessel 142, thus distancing the highly concentrated high velocity cross stream jets 140a-140n from the immediate thrombotic deposit or lesion 144 and/or the wall of the blood vessel 142 and thereby minimizing potential blood vessel wall damage. The cross stream jets 140a-140n traversing between the outflow orifice 22 and the inflow orifice 24 combine to offer an enhanced broad cross section ablation area, such area having a breadth substantially larger and having more concentrated force than prior art devices using multiple inflow and outflow orifices where cross streams are of diminished force and breadth. Having a concentrated flow combining cross stream jets 140a-140n offers selective and directed ablation to take place. Prior art devices using multiple inflow and outflow orifices and having multiple flow areas generate cross streams which are equally weak in all directions, as the flow force is divided between the multiple flow streams, whereby ablation forces cannot be concentrated where desired. The distal end of the smooth catheter tube 20 can be rotated axially to direct the cross stream jets 140a-140n about a longitudinal axis to have 360° coverage or can be rotated axially to offer coverage partially about the longitudinal axis, as required.

The placement of the guidewire 141 within or the removal of the guidewire 141 from the enhanced cross stream mechanical thrombectomy catheter with backloading manifold 10 influences the operation of an embodiment of the present disclosure. Suitably strong and well directed ablation flow can take place with a guidewire 141 extending the full length of the enhanced cross stream mechanical thrombectomy catheter with backloading manifold 10 and/or additionally extending in a distal direction beyond the flexible tapered tip 26 and along the vasculature. Such ablation flow can be further improved, enhanced, modified or otherwise influenced by varying the location of or by full removal of the guidewire 141. With reference to FIG. 10, the guidewire 141, as shown, allows suitable transition of the high velocity fluid jets 136a-136n through the outflow orifice 22 to form cross stream jets 140a-140n which return via the inflow orifice 24. If, for example, the guidewire 141 is urged proximally to a guidewire end position 141a between the inflow orifice 24 and the outflow orifice 22, the inflow orifice 24 is totally unrestricted and has less flow resistance, thereby allowing greater and more forceful ingress of the cross stream jets 140a-140n laden with ablated thrombotic particulates 146, whereas the flow through the outflow orifice 22 remains substantially constant. Urging the guidewire 141 further in a proximal direction to a guidewire end position 141b distal to the outflow orifice 22 causes the outflow orifice 22 and the inflow orifice 24 both to be totally unrestricted and both to have less flow resistance, thereby allowing greater and more forceful flow from the outflow orifice 22, as well as resultantly increased ingress of the cross stream jets 140a-140n laden with ablated thrombotic particulates 146 through the inflow orifice 24. Each of the examples given herein where the guidewire 141 is not totally removed from the smooth catheter tube 20 or other proximally located regions promotes sustained maceration of the loitering entrained ablated thrombotic particulates 146 where the smaller ablated thrombotic particulates 146 are exhausted proximally through the smooth catheter tube 20, the braided catheter tube 18, and the associated and pertinent structure proximal thereto. In another example, urging of the guidewire 141 to a position proximal of the proximal end of the braided catheter tube 18 or total removal of the guidewire 141, in addition to allowing total unrestricted flow through the outflow orifice 22 and the inflow orifice 24, allows unrestricted flow of ablated thrombotic particulates 146 along the smooth catheter tube 20, the braided catheter tube 18, and the associated and pertinent structure proximal thereto.

Although the illustrated cross stream mechanical thrombectomy catheter incorporates an inflow orifice 24 and an outflow orifice 22 aligned to the high pressure tube 71, one or both of the inflow or outflow orifices may be located so that they do not align with the high pressure tube; in this case, other means for guiding a guidewire past the orifice(s) is provided to prevent the guidewire from inadvertently passing through the non-aligned orifice(s).

Figure 12:
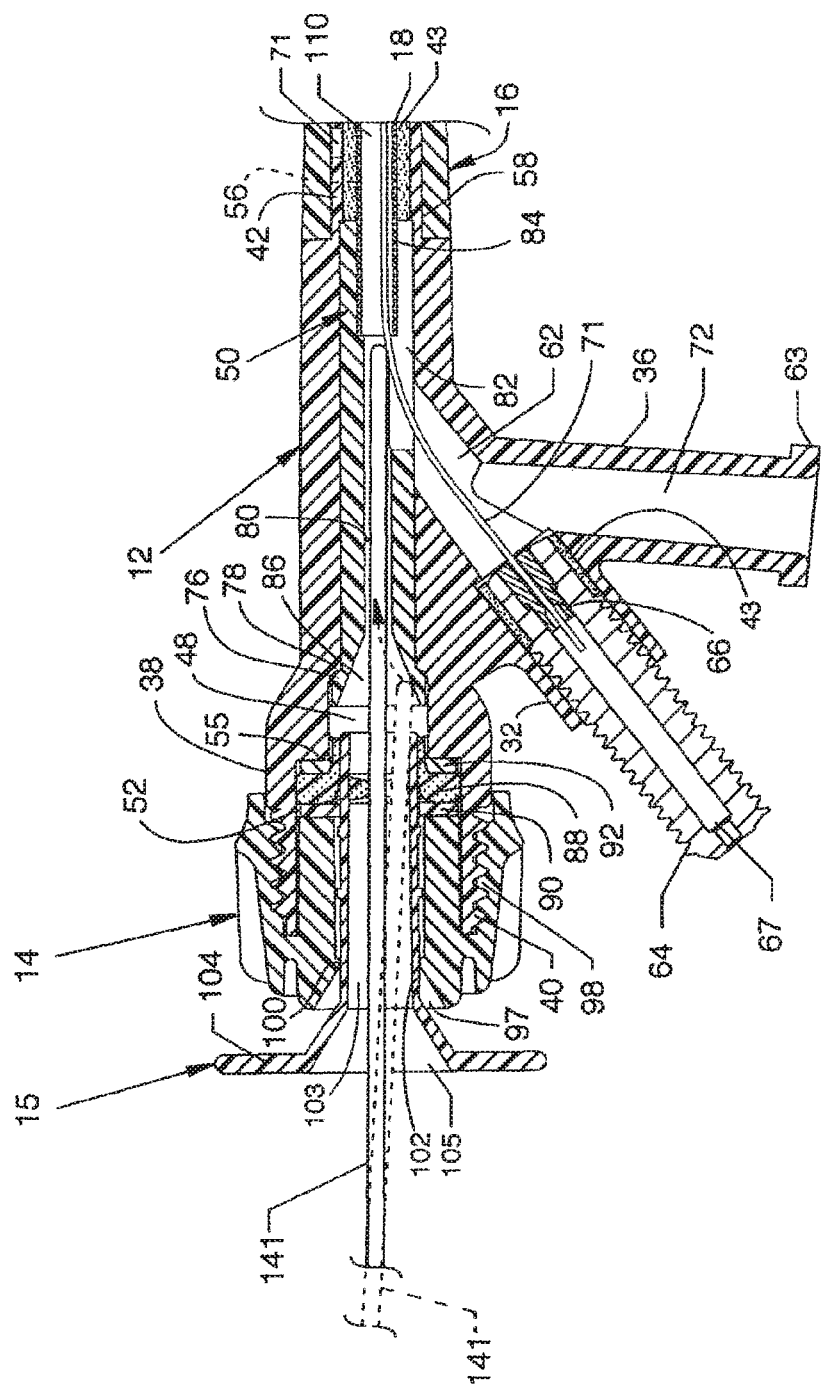
FIG. 12 is a side view in cross section illustrating the introduction of a guidewire into the cross stream mechanical thrombectomy catheter with backloading manifold.

FIG. 12 is a side view in cross section illustrating the introduction of the guidewire 141 into the enhanced cross stream mechanical thrombectomy catheter with backloading manifold 10. When it is desired to remove a guidewire, such as guidewire 141, or exchange guidewires having different attributes, backloading is facilitated by the structure of the insert 50. Loading can be accomplished, if necessary, using the introducer 15 to gain entry through the self-sealing hemostatic valve 88 where the introducer parts the sealing structure of the self-sealing hemostatic valve 88 to allow entry of the guidewire 141 therethrough. Otherwise the guidewire can pass unaided through the self-sealing hemostatic valve 88. The tip of the guidewire may not be in proper alignment with the central passageway 80, such as is shown by the guidewire 141 shown in dashed lines. In such case, impingement of the tip of the distally urged guidewire 141 with the conically-shaped beveled surface entrance 86 of central passageway 80 directs the tip of the guidewire 141 to align with and to be engaged within the central passageway 80 of the insert 50 and to be in alignment, as shown, within the central passageway 80 so as to align with and be subsequently engaged within the proximal portion of the braided catheter tube 18 for passage therethrough. Distal urging of the guidewire 141 also positions the tip of the guidewire 141 for passage through the distal region of the smooth catheter tube 20 where the geometry helpfully accommodates such passage by and along the outflow orifice 22 and the inflow orifice 24 and through the fluid jet emanator 116, the support ring 124, and the flexible tapered tip 26. Preferably, the tip of the guidewire 141 is dome-shaped. Such a dome shape is easily guided by and accommodated by the proximally-facing rounded surface of the terminated loop 117 of the fluid jet emanator 116. Use of the introducer 15 can also be utilized if front loading of a guidewire is required for passage through the self-sealing hemostatic valve 88. Preferably, the guidewire 141 exhibits sufficient size, flexibility and other attributes to navigate the tortuous vascular paths, but exhibits sufficient rigidity not to kink, bend or otherwise be permanently deformed and to stay within the appropriate confines of the distal portion of the smooth catheter tube 20 and not stray through the outflow orifice 22 or the inflow orifice 24. The cross sections of the outflow orifice 22 and the inflow orifice 24 are such that entry thereinto of the horizontally aligned guidewire of sufficient size and larger cross section profile is next to impossible. Notwithstanding, the use of one pair of inflow and outflow orifices further reduces the chance of inadvertent exiting of the guidewire tip through an orifice. This is just one illustrative thrombectomy catheter. Other thrombectomy catheters are described in commonly assigned U.S. Pat. Nos. 8,998,843 and 9,078,691, which are herein incorporated by reference.

As described herein, it may be desirable to provide a thrombectomy catheter with an accessory device to facilitate the removal of older thrombus, which may be harder than an acute thrombus, or the removal of areas of large clot burden. It is contemplated that the accessory device may be a guidewire based device that may be inserted through a guidewire lumen or aspiration lumen of a thrombectomy catheter. The accessory devices may be considered tissue disrupters. They may include various cages, shapes, bumps, unique bends, inverted umbrellas, mixers, blenders, bent guidewires with or without distal cages, deflectors, propellers for mixing, coils, grabbers with fingers, serrated grabbers, offset rotating masses, or combinations thereof. Each of these devices may be operated in a pecking motion, dragging motion, and/or rotationally either via a motor or manually. The accessory devices may help aid in the disruption of the clot or maceration which may then increase the effective removal when combined with the evacuative and shearing properties of a thrombectomy catheter. The accessory devices may also eloquently and simply deflect the catheter tip in a controlled manner which may increase the diametrical zone of disruption and removal. Some of the accessory devices may also be configured to center the thrombectomy catheter. This may keep the accessory device and/or thrombectomy catheter from riding in the same continual path or up against the wall. Riding against the vessel wall especially in a forceful manner may lead to tissue dissection or damage.

In some instances, a guidewire with a predetermined bend placed at a particular distance from the floppy distal tip may be used in combination with a thrombectomy catheter. The location and degree of curvature of this bend may dictate the amount of deflection of the catheter in which the guidewire resides. The bend location and wire design may also dictate the amount or length of floppy wire emanating from the distal tip of the catheter, such as the catheter 10 described herein. Additionally, a rotatable control handle may be provided at the proximal end of the wire to ergonomically enable the user to rotate the wire to generate a circular sweeping action to gain greater coverage within a larger vessel and/or to manipulate the path of the catheter 10. This may help to keep the thrombectomy catheter from riding in the same continual path or up against the vessel wall. The handle may also be used to advance or retract the wire to control the placement and/or magnitude of the diametrical bend of the catheter tip.

Figure 13:
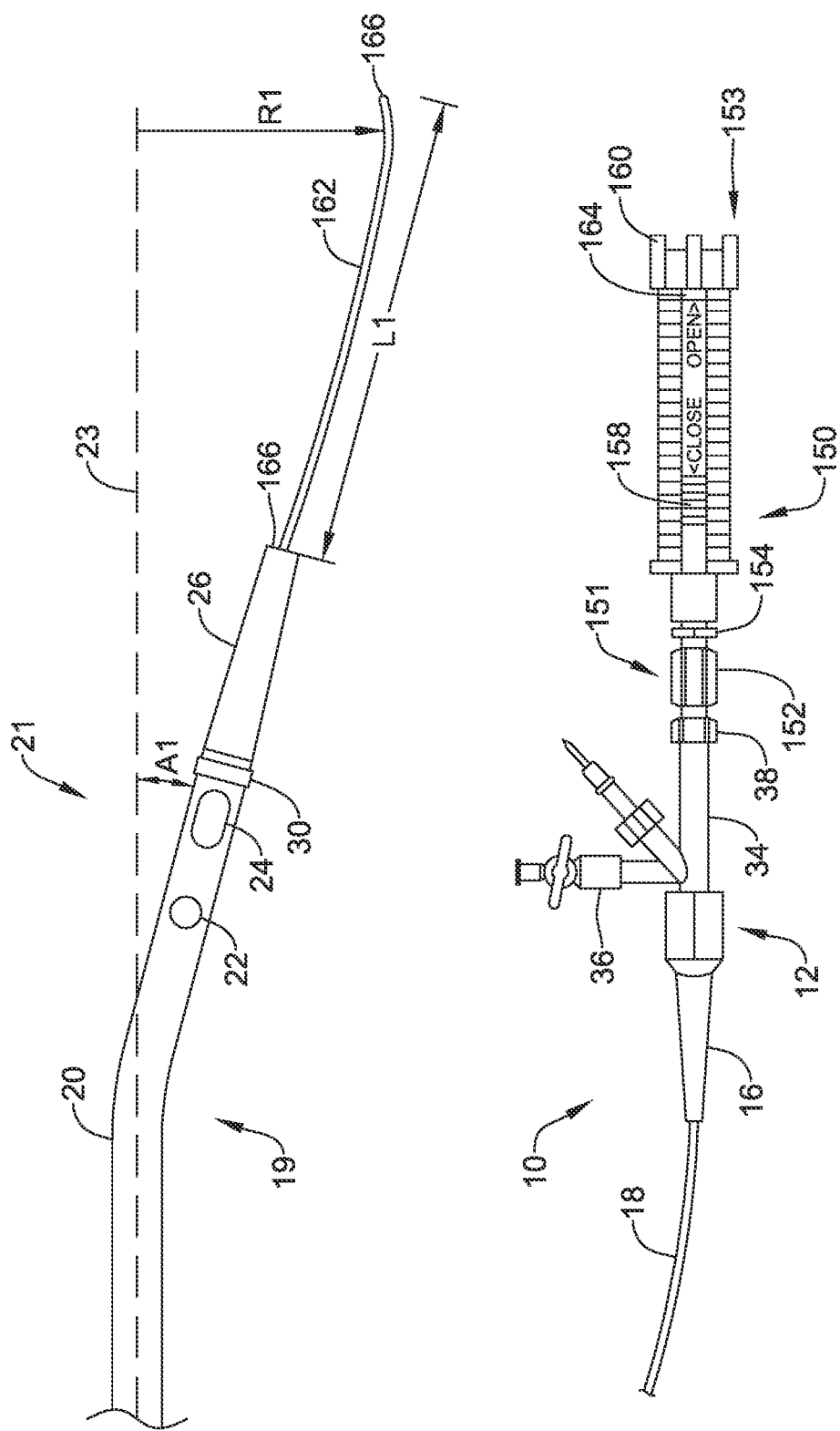
FIG. 13 is a side view of a distal end region of an illustrative guidewire and thrombectomy catheter with an illustrative control handle in a first configuration.
Figure 14:
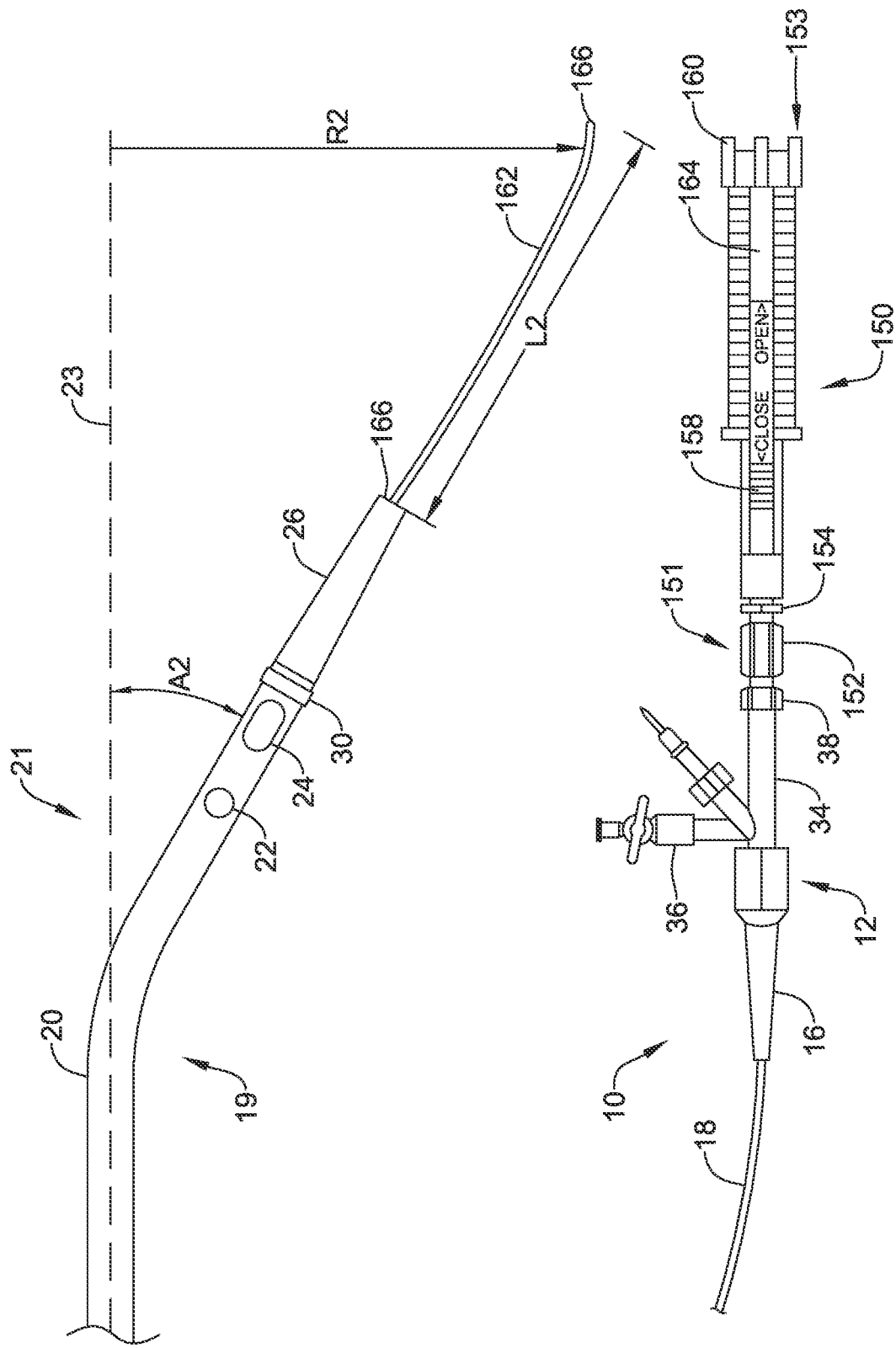
FIG. 14 is a side view of distal end region of an illustrative guidewire and thrombectomy catheter with an illustrative control handle in a second configuration.

A side view of an illustrative rotatable control handle 150 coupled with the manifold 12 of the illustrative thrombectomy catheter 10 in a first configuration and a second configuration, are illustrated in FIGS. 13 and 14, respectively. The rotatable control handle 150 may have a proximal end 153 and a distal end 151 for connecting the handle 150. In some instances, the control handle 150 may be connected to the manifold 12 through a rotatable Luer connector 152. It is contemplated that the rotatable Luer connector 152 may secure the handle 150 to the manifold 12 while allowing for rotation of the control handle 150 relative to the manifold 12. While the connector 152 is described as a Luer connector, it is contemplated that any connector that allows the handle 150 to rotate relative to the manifold 12 may be used. Such a rotatable connection may allow the guidewire 162 (or other accessory device) to rotate independent of the thrombectomy catheter 10 such that the guidewire 162 may be used to facilitate dislodgment of a thrombus, lesion, plaque, etc. It is contemplated that in some embodiments, the handle 150 may not rotate relative to the manifold 12. A variety of coupling mechanisms may be used to secure the Luer connector 152 to the manifold, including, but not limited to, press fittings, snap fittings, mating threads and grooves, etc. A second Luer connector 154 may couple the rotatable Luer connector 152 to the handle positioning slide 158. While not explicitly shown, the rotatable Luer connector 152, Luer connector 154, and handle positioning slide 158 may each include a lumen for receiving a guidewire 162, or other accessory device, therethrough. The handle positioning slide 158 may be slidably disposed within a handle body 156 such that the slide 158 and/or the body 156 may slide relative to one another. For example, FIG. 13 illustrates the handle 150 in a first, or fully distally advanced, configuration and FIG. 14 illustrates the handle 150 in a second, or fully proximally retracted configuration. In some instances, the handle slide 158 and/or the handle body 156 may include stop features configured to limit the retraction and/or advancement range (e.g., proximal and/or distal movement) of the handle slide 158 and/or the handle body 156. The handle 150 may further include a wire collet 164 disposed within a lumen of the handle positioning slide 158. The wire collet 164 may be configured to secure a distal end (not explicitly shown) of the guidewire 162 to the handle 150. This may allow the guidewire 162 to move in concert with the handle 150 (e.g., longitudinally and/or rotationally). The handle 150 may further include a rotating lock nut 160. The lock nut 160 may releasably secure the wire collet to the handle body 156. In some instances, the lock nut 160 may include an aperture to allow the guidewire 162 to be freely moved and/or exchanged.

In the fully advanced configuration, as shown in FIG. 13, the guidewire 162 has a first length L1 extending distally beyond the flexible tapered tip 26 of the thrombectomy catheter 10. It should be noted that for illustrative purposes only, the smooth catheter tube assembly 19 and the guidewire 162 in FIGS. 13 and 14 are illustrated in a larger scale than the braided catheter tube 18, manifold 12 and handle assembly 150. As described herein, the guidewire 162 may have predetermined bend 170 (see, for example, FIG. 15) placed at a distance D from the distal tip 166. The bend 170 may be positioned between a proximal portion 167 and a distal portion 169 of the guidewire 162 such that a proximal portion 167 of the guidewire 162 extends along a longitudinal axis 171 and a distal portion 169 of the guidewires 162 extends an angle θ to the longitudinal axis 171. The bend 170 may be longitudinally positioned on the guidewire 162 such that when the handle 150 is in the fully advanced configuration (FIG. 13), the bend 170 is disposed within a lumen (e.g., the lumen 112 of the smooth catheter tube 20) of the thrombectomy catheter 10, although this is not required. It is further contemplated that the location of the bend 170 relative to the tapered tip 26 of the catheter 10 may be further controlled by manipulating where along the length of the guidewire 162 the handle assembly 150 is coupled to the guidewire 162. For example, the bend 170 may be positioned at a more proximal location within the catheter 10 by allowing a greater length of the guidewire 162 to extend proximally from the control handle 150.

When in the fully advanced configuration (FIG. 13), a first length L1 of the guidewire 162 may extend distally beyond the flexible tapered tip 26 of the thrombectomy catheter 10. The bend 170 in the guidewire 162 may deflect a distal end region 21 of the thrombectomy catheter 10 by a first angle A1 relative to a longitudinal axis 23 of the catheter tube 18 proximal to the bend 170 in the guidewire 162. For example, the bend 170 may bias the portion of the catheter tube 18 that is distal to the bend 170 towards a location offset from the longitudinal axis of the portion of the catheter tube 18 that is proximal to the bend 170 (e.g., towards a vessel wall or thrombus). Deflecting the distal end region 21 of the catheter 10 may increase the diametrical sweep coverage R1 of the distal end region and/or guidewire 162 relative to when no bend 170 is present in the guidewire 162. In other words, as the diametrical sweep coverage R1 increases, the larger a circle the distal end 166 of the guidewire 162 will make when it is rotated. In some cases, the distal end 166 of the guidewire 162 end to the vessel wall (e.g., cover 100% of the vessel diameter) and/or be rotated 360° around the circumference of the vessel. However, the sweep coverage may be less than a complete circle (e.g., less than 360° of rotation) or may not extend to the vessel wall. In other words, the sweep coverage may be less 100% of the diameter and/or circumference of the vessel lumen. As the deflection angle increases, the sweep coverage of the distal end region 21 and/or guidewire 162 may also increase. Additionally, deflection of the distal end region 21 may also bring the inflow orifice 24 and jets 140 closer to the thrombus to further facilitate removal of the tissue.

Proximal retraction of the handle body 156, as shown in FIG. 14, may proximally retract the guidewire 162 such that a second length L2 of the guidewire 162 extends distally beyond the flexible tapered tip 26 of the thrombectomy catheter 10. The second length L2 may be less than the first length L1. It is contemplated that the handle 150 may be used to place the guidewire distal end or tip 166 in any location between the fully extended and fully retracted positions shown in FIGS. 13 and 14, respectively. As the guidewire 162 is proximally retracted, the predetermined bend 170 in the guidewire 162 is also proximally retracted within the lumen (e.g., the lumen 112 of the smooth catheter tube 20) of the thrombectomy catheter 10. The greater the distance between the tapered tip or distal end 26 of the thrombectomy catheter 10 and the bend 170 in the guidewire 162, the greater the deflection angle of the distal end region 21 may be. It is contemplated that the deflection angle A1 in the fully advanced handle configuration (FIG. 13) may be smaller than the deflection angle A2 in the fully retracted handle configuration (FIG. 14). For example, FIG. 14 illustrates that the thrombectomy catheter 10 may be deflected by a second angle A2, which may be larger than the first angle A1. Thus, the sweep coverage R2 of the device when the handle is in the fully retracted configuration (FIG. 14) may be greater than the sweep coverage of the device when the handle is in the fully advanced configuration (FIG. 13). In other words, when rotated, the distal end region 21 of the device 10 may come into contact with a greater cross-section of the vessel when the handle 150 and/or guidewire 162 is in a retracted configuration. It is contemplated that the guidewire 162 may be manipulated without the use of control handle 150. For example, the guidewire 162 may be moved proximally and/or distally and/or rotated through manipulation of the proximal end of the guidewire 162 without the use of control handle 150.

Figure 15:
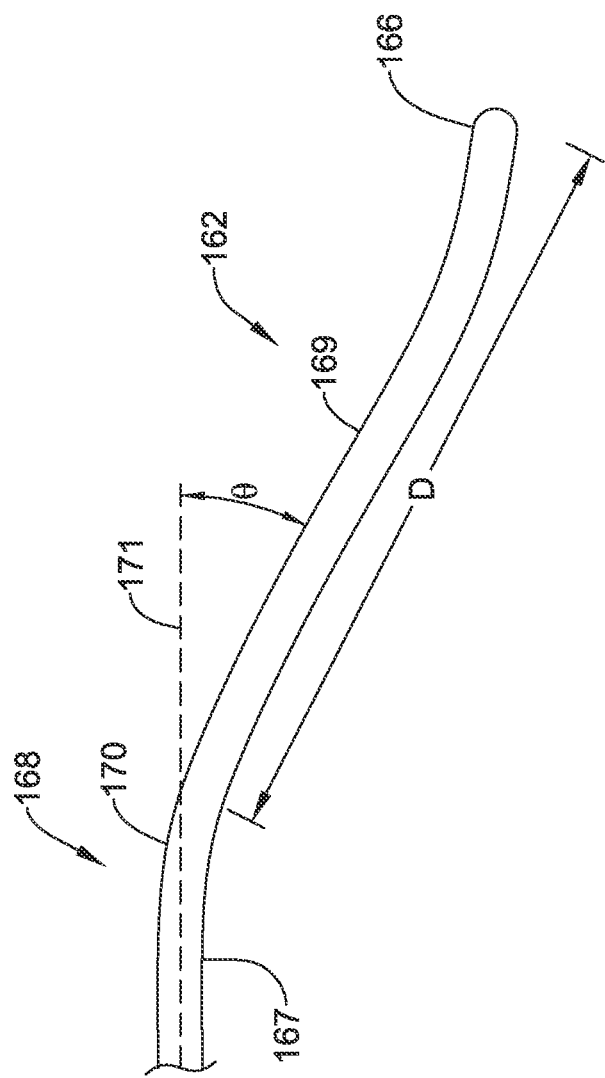
FIG. 15 is a schematic side view of a distal end region of an illustrative guidewire having a bend formed therein.

FIG. 15 illustrates a schematic side view of a distal portion 168 of the illustrative guidewire 162 having a predetermined bend 170. The bend 170 may have a generally smooth curve (e.g., a large radius of curvature) to create a gradual bend in the guidewire 162. In some cases, the radius of curvature of the bend may be in the range of 1 to 2 millimeters or about 1.5 millimeters.

The bend 170 may be positioned a distance D from the distal end 166 of the guidewire 162. In some instances, the bend 170 may be positioned in the range of 0.5 to 20 cm, in the range of 3 to 17 cm, in the range of 7 to 15 cm, in the range of 11 to 13 cm, or approximately 12.5 cm from the distal end 166. However, it is contemplated that the bend 170 may be positioned less than 0.5 cm or more than 20 cm from the distal end 166 as desired. The bend angle θ may be in the range of 1° to 90°, in the range of 10° to 50°, in the range of 15° to 25°, or approximately 20°. However, it is contemplated that the bend angle may be less than 1° or greater than 90°, as desired. In some cases, the bend angle θ may be selected to achieve a desired sweep coverage.

The guidewire 162 may include an elongate shaft or core wire having a proximal end configured to remain outside the body and a distal end 166. In some instances, the proximal end may have a marker or indictor to provide the user with information related to the circumferential location of the bend 170 (e.g., to provide a visual indication of which direction the bend 170 is angled towards). A coil may be disposed over a length of the core wire adjacent to the distal end. A tip having a generally curved, atraumatic, shape, such as a solder tip, may be formed on the core wire at or adjacent to the distal end. A portion of the coil may be coupled to the tip. In some instances, a portion of the coil may be embedded within the tip. Embedded is understood to be disposed within, coupled to, set in, implanted, fixed, etc. The tip may, thus, fix the coil relative to core wire. Alternatively, the coil may be soldered to core wire proximate to the tip. In some instances, the coil may be replaced with a slotted tube or other flexible member.

The core wire may be comprised of nickel-titanium alloy, stainless steel, a composite of nickel-titanium alloy and stainless steel, and/or include nickel-cobalt-chromium-molybdenum alloy (e.g., MP35-N). Alternatively, the core wire may be comprised of metals, polymers, combinations or composites thereof, or other suitable materials. In some instances, a portion or all of the guidewire may be radiopaque to allow the guidewire to be viewed on a fluoroscopy screen, or other imaging technique, during a procedure. In some instances, the distal end and/or coil may be radiopaque to aid the physician in determining the location of the distal end of the core wire.

The core wire may be distally tapered. For example, the core wire may include a plurality of distal segments or comprise a single, generally tapered distal end. Each distal segment may comprise a decreased outside diameter or individual segments may each taper along the length of a particular segment. A person of ordinary skill in the art could appreciate that a vast number of alternate configurations of segments and distal ends may be included without departing from the scope of the invention.

The guidewire 162 may have a stiffness that is less than the braided catheter shaft 18, but greater than the smooth catheter portion 20. This may prevent the proximal portion of the catheter shaft 18 from deflecting while allowing the distal portion of the catheter shaft 20 to be deflected by the predetermined bend 170. In other words, the braided catheter shaft 18 may be sufficiently strong to overcome the biasing force of the bend 170 in the guidewire while the guidewire 162 may be sufficiently strong to overcome the biasing force of the smoother catheter portion 20.

In some instances, a splittable sheath 180 may be used to facilitate the introduction of the guidewire 162 and/or any other accessory device into a lumen of the thrombectomy catheter 10, as illustrated in FIGS. 16-20. The splittable sheath 180 may have a proximal handle portion 182 and a distal portion 184. The handle portion 182 may include a first flange 186 and a second flange 188 extending in opposite directions from one another. The distal portion 184 of the splittable sheath 180 may be sized to fit snugly within a lumen (e.g., the cavity 46 or the cavity 48 illustrated in FIG. 3) of the cavity body 38 of the manifold 12. The distal end portion 184 may be tapered or thinned such that there is no leading "shoulder" during insertion to the manifold 12, although this is not required. The splittable sheath 180 may also include a region of longitudinal weakness 190 for splitting the handle 182, which also extends toward the distal end 184, allowing for splitting of the sheath 180 along its entire length.

Figure 16:
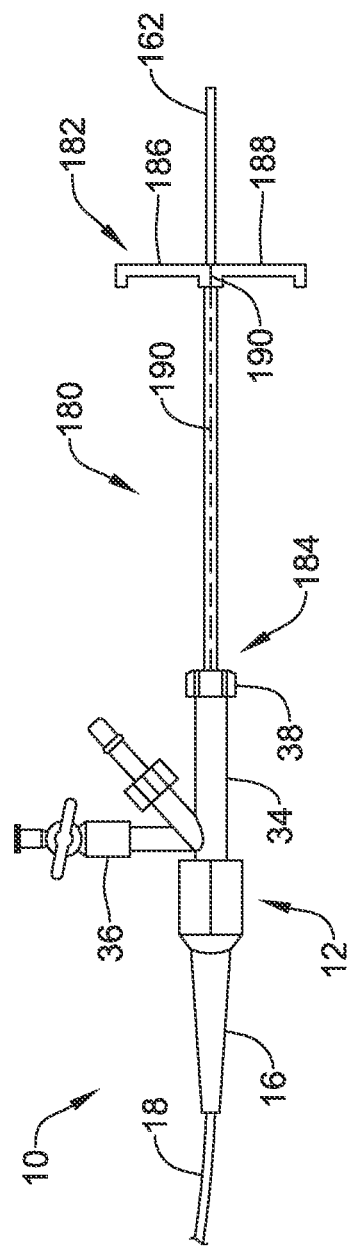
FIGS. 16-20 illustrate an illustrative method for loading a guidewire into an illustrative catheter.
Figure 17:
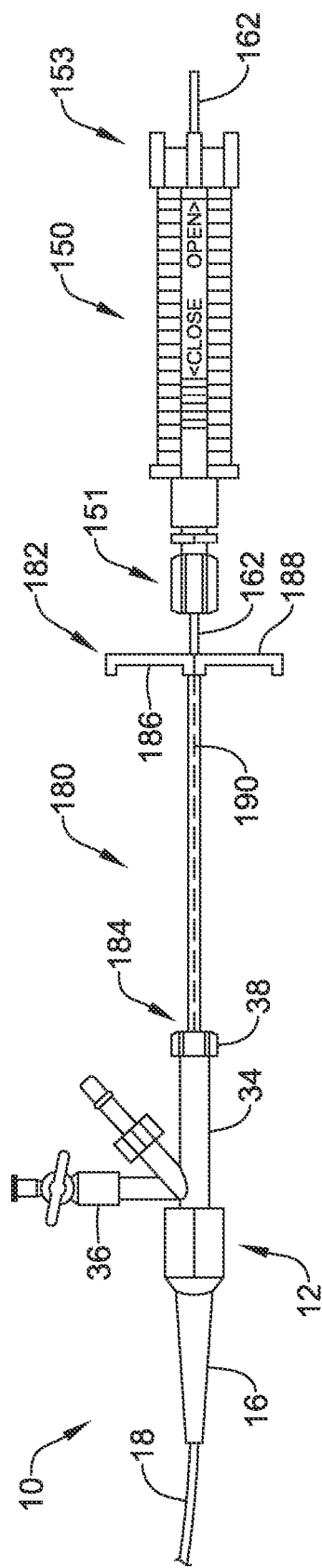
Figure 18:
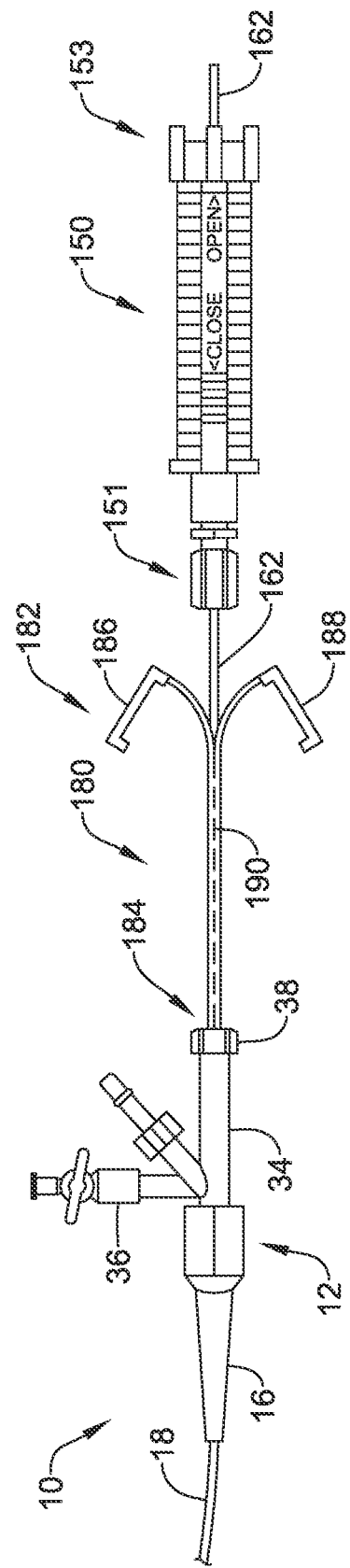
Figure 19:
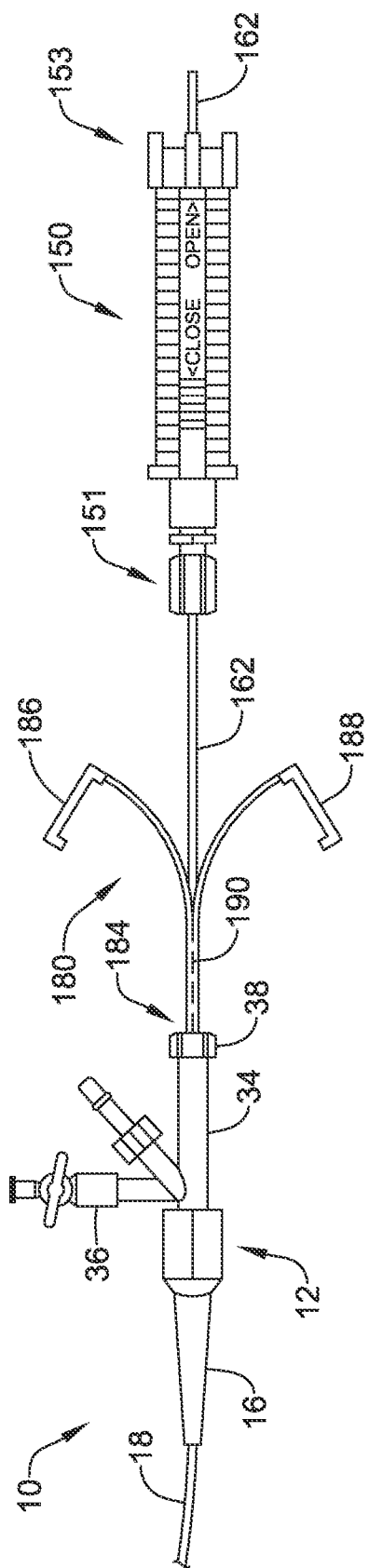
Figure 20:
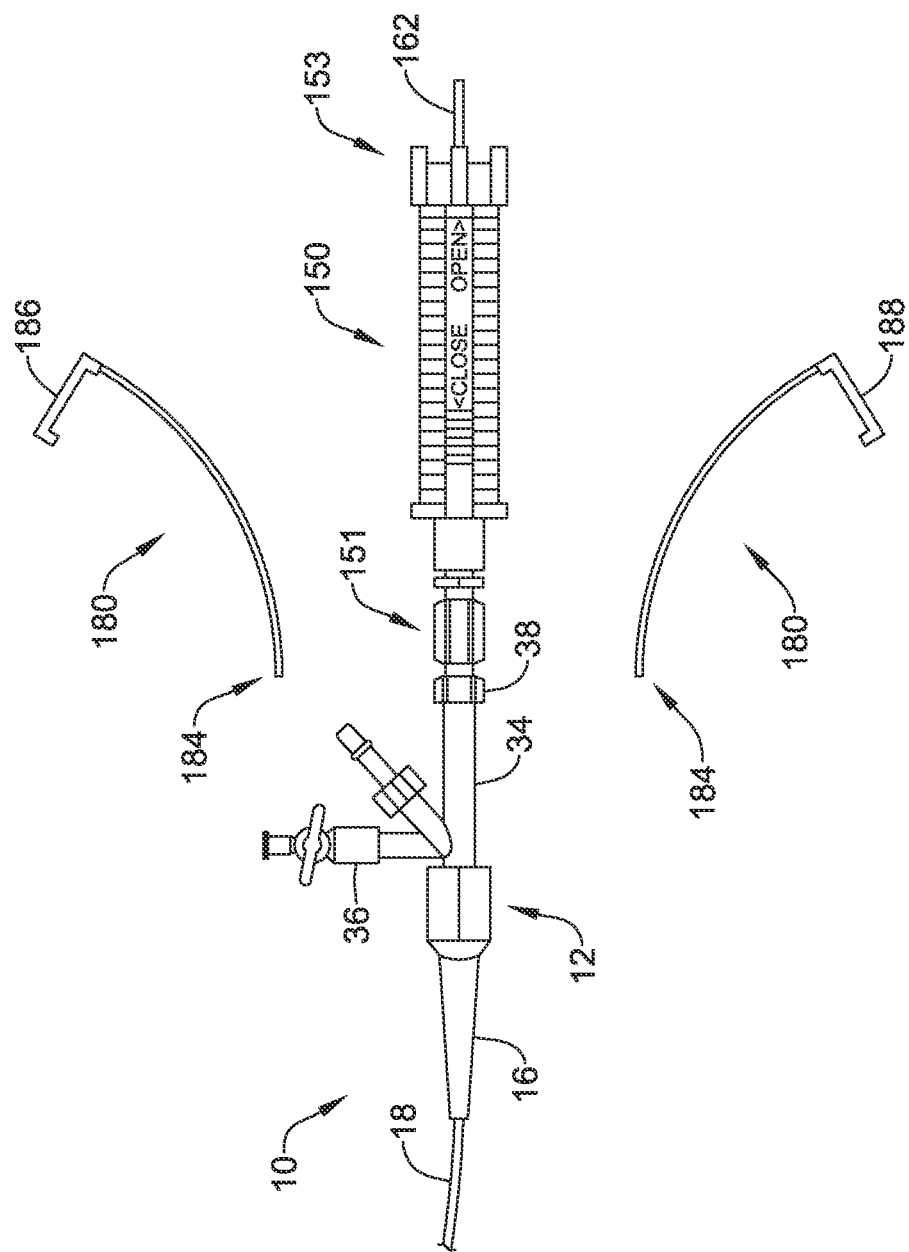

A distal end 166 of the guidewire 162, or other accessory device, may be inserted into a lumen of the splittable sheath, as shown in FIG. 16 and distally advanced until the distal end 151 of the handle 150, if so provided, is adjacent to the proximal portion 182 of the sheath 180, as shown in FIG. 17. The splittable sheath 180 may then be split along the region of longitudinal weakness 190 to allow the guidewire 162 to be further advanced in the distal direction, as shown in FIGS. 18 and 19. It is contemplated that once the guidewire 162 is disposed far enough into the device 10 that it shouldn't be accidentally retracted, the splittable sheath 180 may be disengaged from the manifold 12, although this is not required. As the guidewire 162 is further advanced, the splittable sheath 180 may be fully removed, as shown in FIG. 20. In some instances, the distal end 151 of the handle 150 may be releasably connected to the manifold 12, although this is not required.

Figure 21:
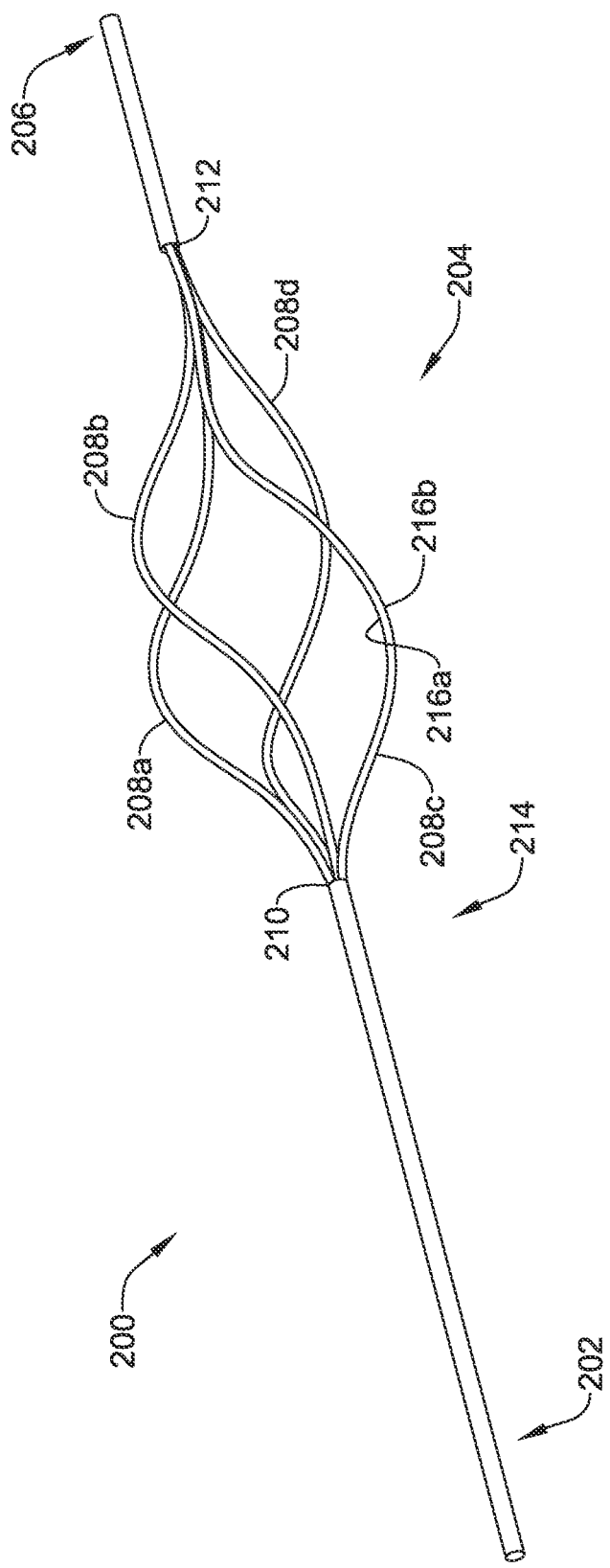
FIG. 21 is a perspective view of an illustrative accessory device.

FIG. 21 illustrates a perspective view of another illustrative accessory device 200 that may be used with a thrombectomy catheter, such as the thrombectomy catheter 10 described herein. The accessory device 200 may include a straight or angled (such as the bent guidewire 162 described herein) guidewire 202 and a cage 204 affixed adjacent to a distal end region 214 of the guidewire 202. The guidewire 202 may be similar in form and function to the guidewire 162 described herein. However, the predetermined bend described herein may or may not be present resulting in an angled or straight guidewire, as desired. The proximal end of the device 200 may be releasably coupled to a control handle, such as the control handle 150 described herein. Use of the control handle 150 may allow the device 200 to be retracted, deployed, and rotated in a controlled manner, although its use is not required.

The cage 204 may comprise a plurality of struts, strands, or groups of wires 208a, 208b, 208c, 208d (collectively, 208). While the cage 204 is illustrated as having four strands 208, it is contemplated that the cage 204 may include any number of strands 208, such as but not limited one, two, three, four, or more, as desired. In some cases, the cage 204 may include twenty or more strands 208. In some instances, each strand 208 may be comprised of two or more individual wires 216a, 216b, although this is not required. In some embodiments, each strand 208 may be formed from a single wire or strut. In other cases, the strands 208 may include up to five or more individual wires per strand 208. The strands 208 and/or wires 216a, 216b may be made from stainless steel or a shape memory material such as, but not limited to nitinol. The stiffness of the strands 208 may be varied as desired. In some instances, the strands 208 may be provided with serrations and/or sharp edges to aid in clot maceration. In some embodiments, the outer most part of the strands 208 may remain smooth since this will be the part that may contact the vessel wall and help center the device.

The strands 208 may be affixed to one another at their proximal ends 210 and distal ends 212. The proximal end 210 may be affixed to the distal end region 214 of the guidewire 202. The distal end 212 may be affixed to a solid or tubular distal extension 206. It is contemplated that the distal extension 206 may facilitate distal advancement of the device 200 through a lesion. The strands 208 may have a generally spiral or helical pattern extending from the proximal end 210 to the distal end 212, although this is not required. For example, the proximal end 210 and the distal end 211 of a given strand 208 may be circumferentially offset from one another. It is contemplated that different spiral patterns could be used to aid in clot maceration. The strands 208 may be evenly spaced or eccentrically spaced as desired. While the strands 208 have been described as wires, it is contemplated that the cage 204 may be formed from a cut tube. It is further contemplated that the cage 204 may be self-expanding or include an actuation mechanism to manually deploy the cage 204. The cage 204 may be collapsible into a delivery configuration which may have a smaller cross-sectional area and a longer length than the expanded cage 204 illustrated in FIG. 21.

Figure 22:
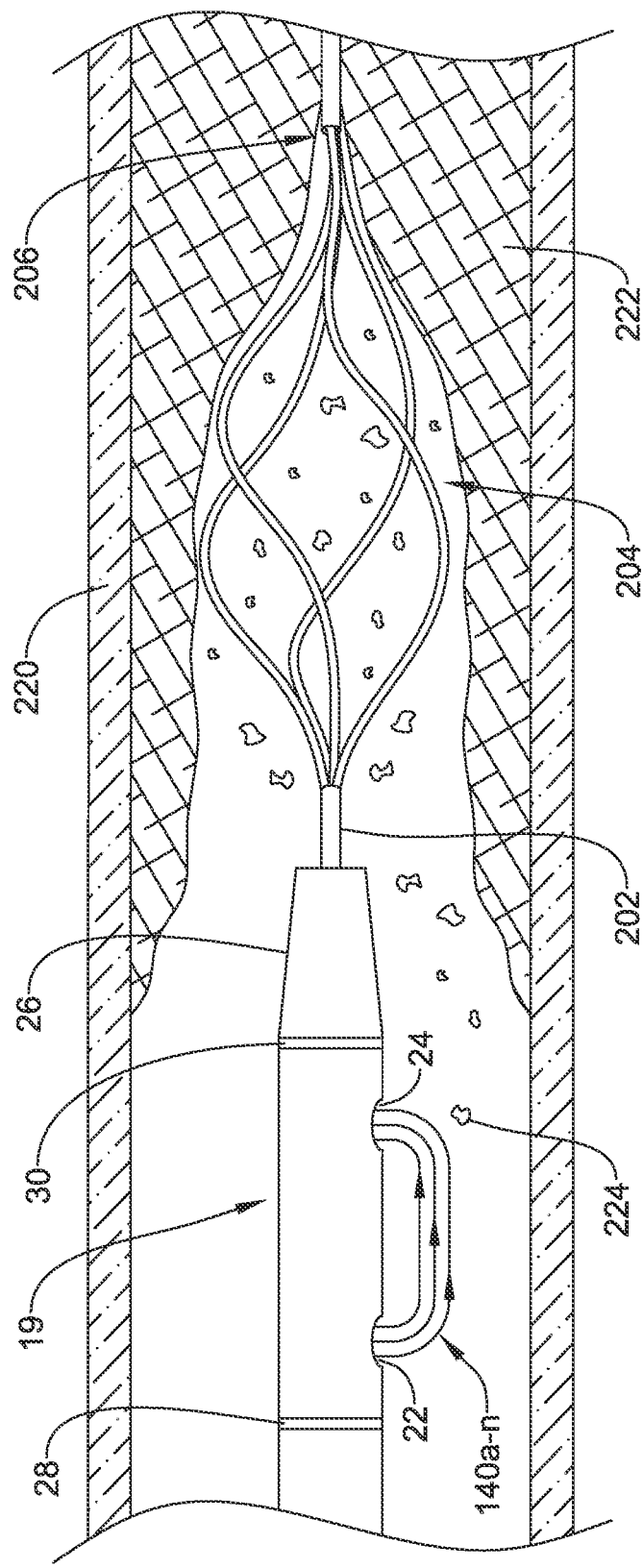
FIG. 22 is a side view in partial cross-section illustrating the accessory device of FIG. 21 with an illustrative catheter in a vessel.

FIG. 22 is a side view of the distal region of the cross stream mechanical thrombectomy catheter 10 showing in particular the distal end of the smooth catheter tube assembly 19 positioned in a blood vessel 220 (shown in cross section) at a site of a thrombotic deposit or lesion 222 with accessory device 200 extending distally therefrom. It is contemplated that the device 200 may be loaded into a lumen of a thrombectomy catheter 10 in a similar manner to that described herein with respect to FIGS. 16-20. While FIG. 22 depicts the smooth catheter tube assembly 19 as being in a blood vessel in particular, it is to be understood that it is not limited to use in a blood vessel but has utility with respect to any body cavity in general. High velocity fluid jets (such as jets 136a-136n shown in FIG. 10) of saline or other suitable solution are emanated or emitted in a proximal direction from the fluid jet emanator 116 into the smooth catheter tube 20 and pass through the outflow orifice 22 creating cross stream jets 140a-140n directed toward the wall of the blood vessel 220 having thrombotic deposits or lesions 222 and thence are influenced by the low pressure at the inflow orifice 24 to cause the cross stream jets 140a-140n to be directed distally substantially parallel to the central axis of the blood vessel 220 to impinge and break up thrombotic deposits or lesions 222 and to, by entrainment, urge and carry along the dislodged and ablated thrombotic particulates 224 of the thrombotic deposits or lesions 222 through the inflow orifice 24, a relatively low pressure region, and into the lumen 112, which functions as a recycling maceration lumen or chamber and also as an exhaust lumen. The entrainment through the inflow orifice 24 is based on entrainment by the high velocity fluid jets 136a-136n. The outflow is driven by internal pressure which is created by the high velocity fluid jets 136a-136n and the fluid entrained through the inflow orifice 24.

The accessory guidewire based device 200 with the spiral cage 204 on the distal end may be advanced through the guidewire or aspiration lumen of the thrombectomy catheter 10. The device 200 can be operated in a pecking motion, dragging motion, or manually rotated to help aid in the disruption of the lesion 222. This may increase removal and/or shorten a procedure when combined with the evacuative and shearing properties of the thrombectomy catheter 10. Furthermore, the cage 204 may be retracted, rotated, and deployed with a special handle, as described herein with respect to FIGS. 13 and 14. It is contemplated that the cage 204 may also be driven by a motor (rotationally and/or longitudinally). As described herein, the device 200 may also have a bent guidewire 202 to deflect the distal end region of the thrombectomy catheter 10 relative to a longitudinal axis of the catheter tube 18 proximal to the bend in the guidewire 202. Deflecting the distal end region of the catheter 10 may increase the sweep coverage of the distal end region and/or device 200. For example, as the deflection angle increases, the sweep coverage of the distal end region and/or guidewire 202 may also increase. Additionally, deflection of the distal end region of the catheter 10 may also bring the inflow window and jets closer to the thrombus to further facilitate removal of the tissue. It is contemplated that the accessory device 200 should not cause any additional hemolysis since the shear rate for blood cells is not exceeded in the arrangement.

Figure 23:
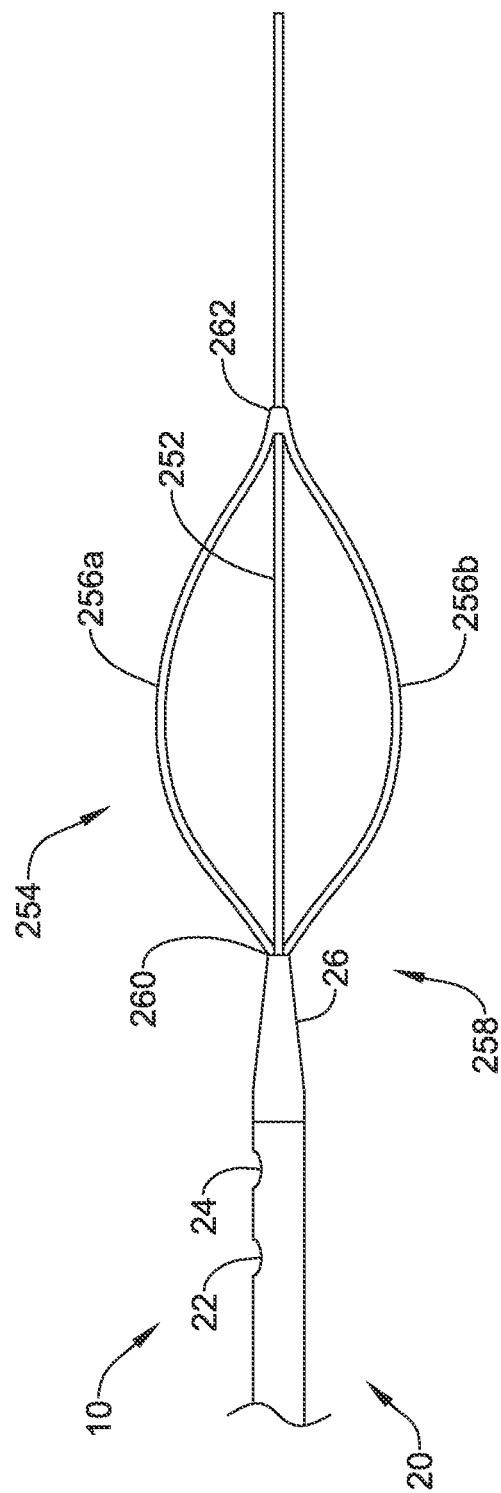
FIG. 23 is a side view of another illustrative accessory device.

FIG. 23 illustrates a side view of another illustrative accessory device 250 that may be used with a thrombectomy catheter, such as the thrombectomy catheter 10 described herein. The accessory device 250 may include a straight or angled (such as the bent guidewire 162 described herein) guidewire 252 and a bi-strut cage 254 attached adjacent to a distal end region 258 of the guidewire 252. The guidewire 252 may be similar in form and function to the guidewire 162 described herein. However, the predetermined bend 170 described herein may or may not be present resulting in an angled or straight guidewire, as desired. The proximal end of the device 250 may be releasably coupled to a control handle, such as the control handle 150 described herein. Use of the control handle 150 may allow the device 250 to be retracted, deployed, and rotated in a controlled manner, although its use is not required.

The cage 254 may comprise two struts 256a, 256b (collectively, 256). While the cage 254 is illustrated as having two struts 256, it is contemplated that the cage 254 may include any number of struts 256, such as but not limited one, two, three, four, or more, as desired. In some instances, each strut 208 may be comprised of two or more individual wires (not explicitly shown), although this is not required. In some embodiments, each strut 256 may be formed from a single wire or strut. The struts 256 may be made from stainless steel or a shape memory material such as, but not limited to nitinol. The stiffness of the struts 256 may be varied as desired. In some instances, the struts 256 may be provided with serrations and/or sharp edges to aid in clot maceration. In some instances, the struts 256 may be formed from cutting blades. In some embodiments, the blades may have one edge that is sharper than the other edge. This may require the device to be rotated in a specific direction to achieve cutting. In some embodiments, the outer most part of the struts 256 may remain smooth since this will be the part that may contact the vessel wall and help center the device.

The struts 256 may be affixed to one another and/or the guidewire 252 at their proximal ends 260 and distal ends 262. It is contemplated that the guidewire 252 may extend distally beyond the distal end 262 of the cage 254 to facilitate distal advancement of the device 250 through a lesion. The struts 256 may each have a generally arced or curved configuration, although other structures are contemplated. The struts 256 may be evenly spaced or eccentrically spaced as desired. For example, the struts 256 may be positioned approximately 180° from one another. It is further contemplated that the cage 254 may be self-expanding or include an actuation mechanism to manually deploy the cage 254. The cage 254 may be collapsible into a delivery configuration which may have a smaller cross-sectional area and a longer length than the expanded cage 254 illustrated in FIG. 23. While not explicitly shown, a spring may be provided on the guidewire 252 between the proximal and distal ends 260, 262 of the cage 254 to bias the cage 254 into the delivery configuration.

The accessory guidewire based device 250 with the bi-strut cage 254 on the distal end may be advanced through the guidewire or aspiration lumen of the thrombectomy catheter 10. The device 250 can be operated in a pecking motion, dragging motion, or manually rotated to help aid in the disruption of the lesion. This may increase removal or shorten a procedure when combined with the evacuative and shearing properties of the thrombectomy catheter 10. Furthermore, the cage 254 may be retracted, rotated, and deployed with a special handle, as described herein with respect to FIGS. 13 and 14. It is contemplated that the cage 254 may also be driven by a motor (rotationally and/or longitudinally). For example, rapid rotation, in the range of 20 to 10,000 rpm may be provided by an externally located motor to macerate the clot. As described herein, the device 250 may also have a bent guidewire 252 to deflect the distal end region of the thrombectomy catheter 10 relative to a longitudinal axis of the catheter tube proximal to the bend in the guidewire 252. Deflecting the distal end region of the catheter 10 may increase the sweep coverage of the distal end region and/or device 250. For example, as the deflection angle increases, the sweep coverage of the distal end region of the catheter 10 and/or guidewire 252 may also increase. Additionally, deflection of the distal end region of the catheter 10 may also bring the inflow orifice or window 24 and jets 140a-140n closer to the thrombus to further facilitate removal of the tissue. It is contemplated that the accessory device 250 should not cause any additional hemolysis since the shear rate for blood cells is not exceeded in the arrangement.

Figure 24:
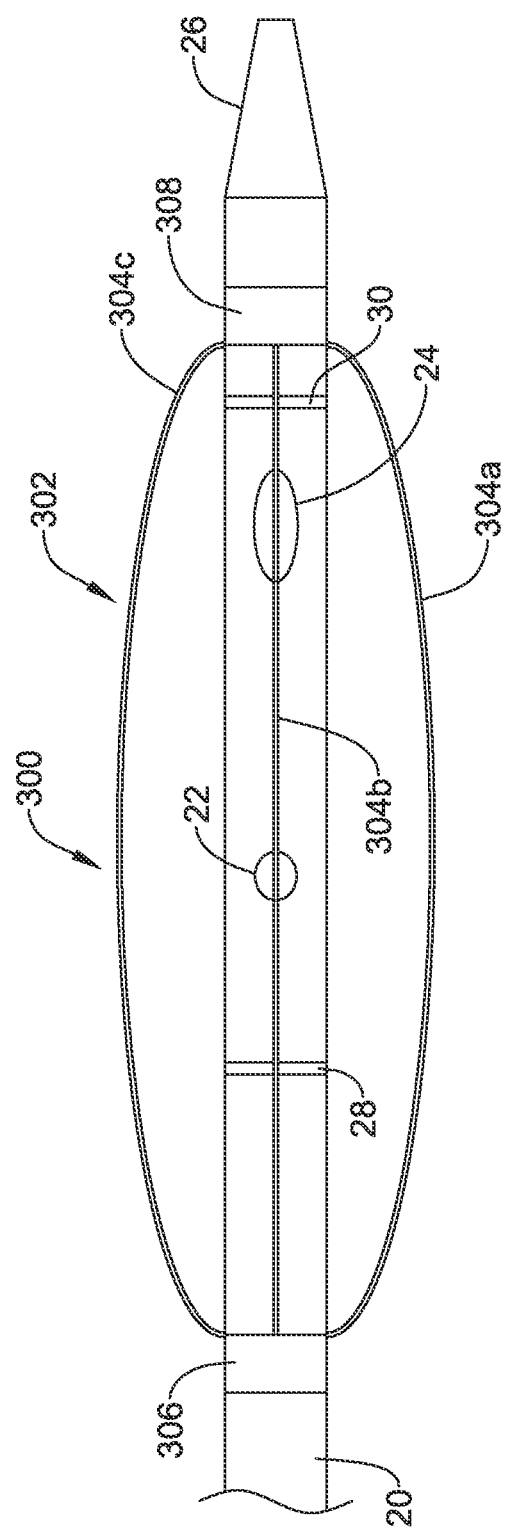
FIG. 24 is a side view of another illustrative accessory device.

FIG. 24 illustrates a side view of another illustrative accessory device 300 that may be used with a thrombectomy catheter, such as the thrombectomy catheter 10 described herein. The accessory device 300 may include an expandable basket 302 positioned over the catheter tube 20 adjacent to the outflow orifice 22 and the inflow orifice 24. The basket 302 may comprise a plurality of longitudinally extending struts 304a, 304b, 304c (collectively, 304). It is contemplated that the basket 302 may include any number of struts 304, such as but not limited one, two, three, four, or more, as desired. In some instances, each strut 304 may be comprised of two or more individual wires (not explicitly shown), although this is not required. In some embodiments, each strut 304 may be formed from a single wire or strut. The struts 304 may be made from stainless steel or a shape memory material such as, but not limited to nitinol. The stiffness of the struts 304 may be varied as desired. In some instances, the struts 304 may be provided with serrations and/or sharp edges to aid in clot maceration. In some embodiments, the outer most part of the struts 304 may remain smooth since this will be the part that may contact the vessel wall and help center the device.

The struts 304 may be affixed to and/or over the catheter tube 20 at a proximal end connection 306 of the basket 302 and a distal end connection 308 of the basket 302. It is contemplated that one of the proximal end connection 306 or the distal end connection 308 may be fixedly secured to the catheter tube 20 while the other connection may be slidably disposed over the catheter tube 20. This may allow the basket 302 to maintain a desired longitudinal positon along the catheter tube 20 while allowing the basket 302 to assume a delivery configuration in which the basket has a smaller cross-sectional area and a longer length than the expanded basket 302 illustrated in FIG. 24.

The struts 304 may be evenly spaced or eccentrically spaced as desired. For example, the struts 304 may uniformly distributed about the circumference of the catheter tube 20, eccentrically distributed, and/or weighted to one side. These are just examples. It is further contemplated that the basket 302 may be self-expanding or include an actuation mechanism to manually deploy the basket 302.

In some instances, the device 300 may be used in combination with a bent guidewire, such as the guidewire 162 described herein. This may deflect the distal end region of the thrombectomy catheter 10 relative to a longitudinal axis of the catheter tube proximal to the bend 170 in the guidewire 162. Deflecting the distal end region of the catheter 10 may increase the sweep coverage of the distal end region of the catheter 10 and/or device 300. For example, as the deflection angle increases, the sweep coverage of the distal end region and/or device 300 may also increase. Additionally, deflection of the distal end region of the catheter 10 may also bring the inflow window 24 and jets 140a-140n closer to the thrombus to further facilitate removal of the tissue. It is contemplated that the accessory device 300 should not cause any additional hemolysis since the shear rate for blood cells is not exceeded in the arrangement.

Figure 25:
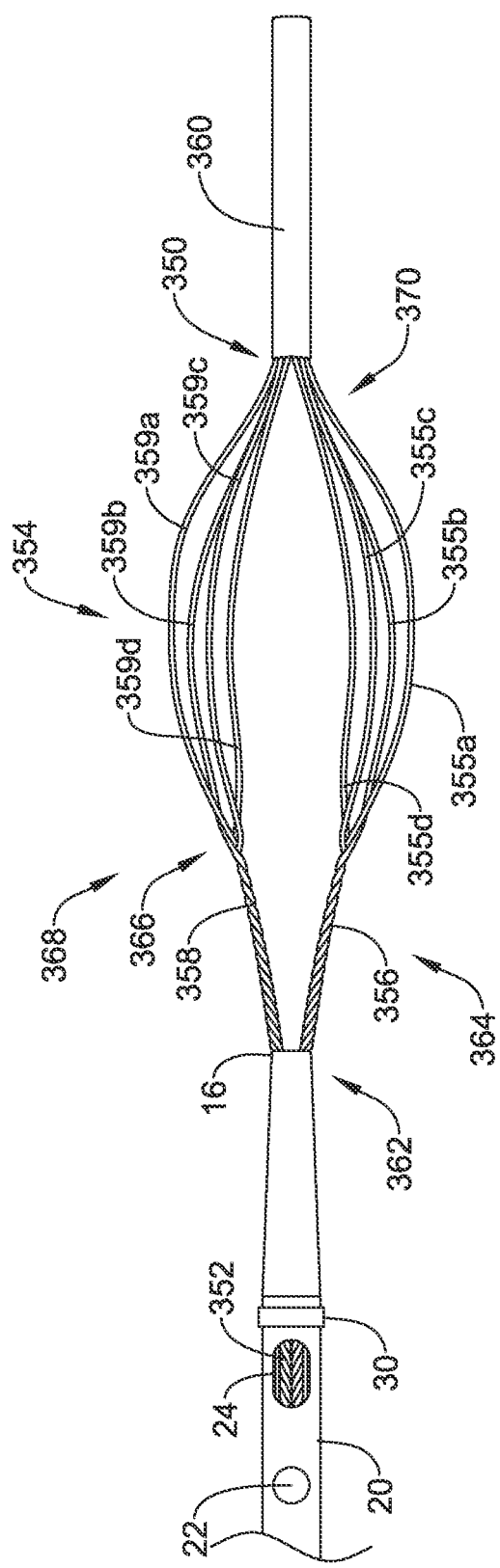
FIG. 25 is a side view of another illustrative accessory device.

FIG. 25 illustrates a side view of another illustrative accessory device 350 that may be used with a thrombectomy catheter, such as the thrombectomy catheter 10 described herein. The accessory device 350 may include a straight or angled (such as the bent guidewire 162 described herein) proximally extending portion 352 and an expandable basket 354. It is contemplated that the proximally extending portion 352 may have a predetermined bend configured to angle a distal portion of the device 350 relative to the longitudinal axis of the device 350 proximal to the bend, although this is not required. The proximal end of the device 350 may be releasably coupled to a control handle, such as the control handle 150 described herein. Use of the control handle 150 may allow the device 350 to be retracted, deployed, and rotated in a controlled manner, although its use is not required.

In some instances, the proximally extending portion 352 may be formed from two longitudinally extending strands 356, 358. The strands 356, 358 may each be formed from a plurality of individual filaments 356a, 356b, 356c, 356d, 358a, 358b, 358c, 358d. It is contemplated that two, three, four, or more individual filaments may be wound, woven, or braided together to form the strands 356, 358. The proximally extending portion 352 may be disposed within a tube, such as polymeric tube, to maintain the strands 356 in close proximity during advancement of the device within the catheter 10. This may facilitate advancement of the device 300, reduce the potential of the device 350 to snag, and/or help with pushablility, among other features. The tube may not extend the entire length of the device. For example, the tube may terminate a location 362 proximal to the distal end of the device 350. This may allow the strands 356, 358 to separate as they are advanced distally beyond the distal end 26 of the catheter 10

The first strand 356 may not be woven or wound along its entire length. For example at location 364, the filaments 356a, 356b, 356c, 356d may be separated and spread apart to form a basket type structure. The filaments 356a, 356b, 356c, 356d may be made from stainless steel or a shape memory material such as, but not limited to nitinol. The material may be selected to allow the filaments to assume an expanded configuration when the basket is deployed. Similarly, the second strand 358 may not be woven or wound along its entire length. For example at location 366, the filaments 358a, 358b, 358c, 358d may be separated and spread apart to form a basket type structure. The filaments 358a, 358b, 358c, 358d may be made from stainless steel or a shape memory material such as, but not limited to nitinol. The material may be selected to allow the filaments to assume an expanded configuration when the basket is deployed. The expandable basket 354 may have a partially closed configuration. For example, the proximal end 368 of the basket 354 may be more "open" than the distal end 370 where filaments 356a, 356b, 356c, 356d, 358a, 358b, 358c, 358d come together. Two large long openings 372a, 372b may extend along the sides of the basket 354 (e.g., each long opening extending between the first filaments 356a, 356b, 356c, 356d, and the second filaments 358a, 358b, 358c, 358d). It is contemplated that the basket 354 may be self-expanding or include an actuation mechanism to manually deploy the basket 354. The basket 354 may be collapsible into a delivery configuration which may have a smaller cross-sectional area and a longer length than the expanded basket 354 illustrated in FIG. 25.

Distal to the distal end 370 of the basket 354, the filaments 356a, 356b, 356c, 356d, 358a, 358b, 358c, 358d may be surrounded by a tube, such as a polymer tube 360 to maintain the filaments in a confined arrangement. The polymer tube 360 may extend distally of the basket 354 to facilitate advancement of the device 300 through a lesion.

The accessory guidewire based device 350 with the expandable basket 354 may be advanced through the guidewire or aspiration lumen of the thrombectomy catheter 10. The device 350 can be operated in a pecking motion, dragging motion, or manually rotated to help aid in the disruption of the lesion. This may increase removal or shorten a procedure when combined with the evacuative and shearing properties of the thrombectomy catheter 10. Furthermore, the basket 354 may be retracted, rotated, and deployed with a special handle, as described herein with respect to FIGS. 13 and 14. It is contemplated that the device 350 may also be driven by a motor (rotationally and/or longitudinally). Deflecting the distal end region of the catheter 10 may increase the sweep coverage of the distal end region of the catheter 10 and/or the accessory device 350.

For example, as the deflection angle increases, the sweep coverage of the distal end region of the catheter 10 and/or basket 354 may also increase. Additionally, deflection of the distal end region of the catheter 10 may also bring the inflow window 24 and jets 140a-140n closer to the thrombus to further facilitate removal of the tissue. It is contemplated that the accessory device 350 should not cause any additional hemolysis since the shear rate for blood cells is not exceeded in the arrangement.

Figure 26:
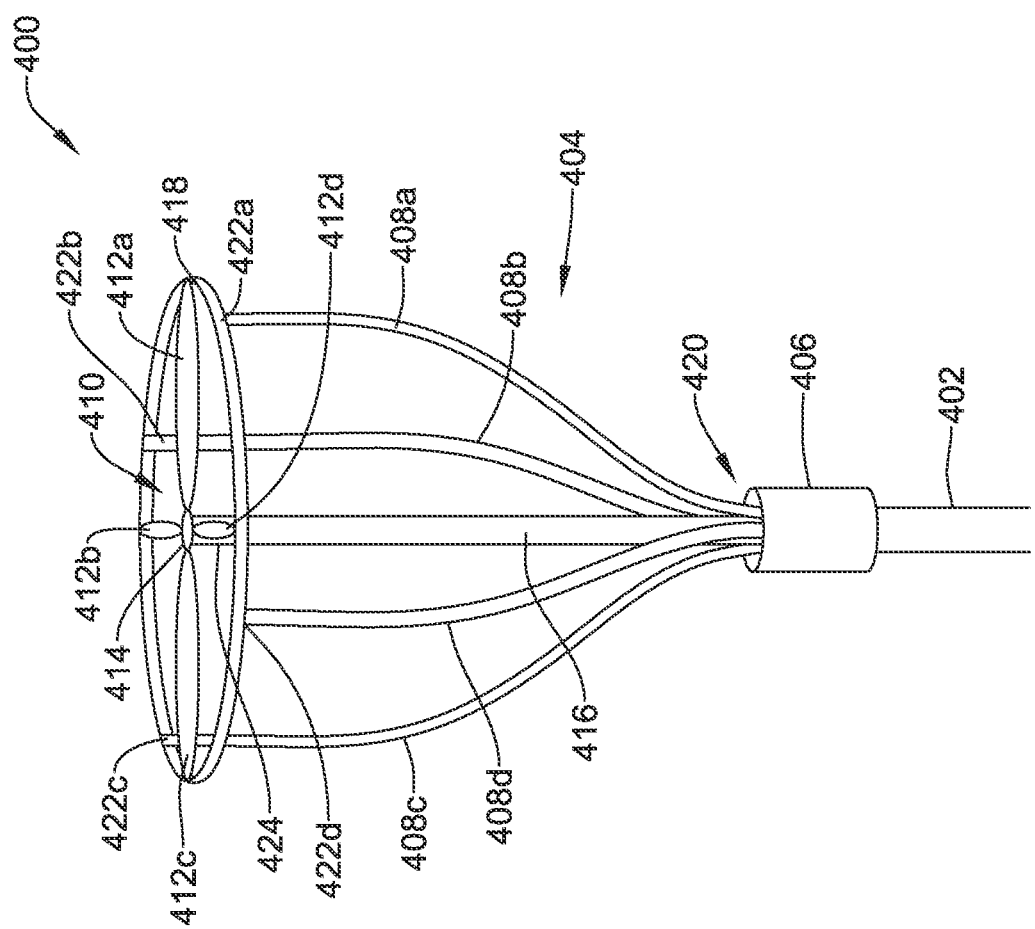
FIG. 26 is a side view of another illustrative accessory device.
Figure 27:
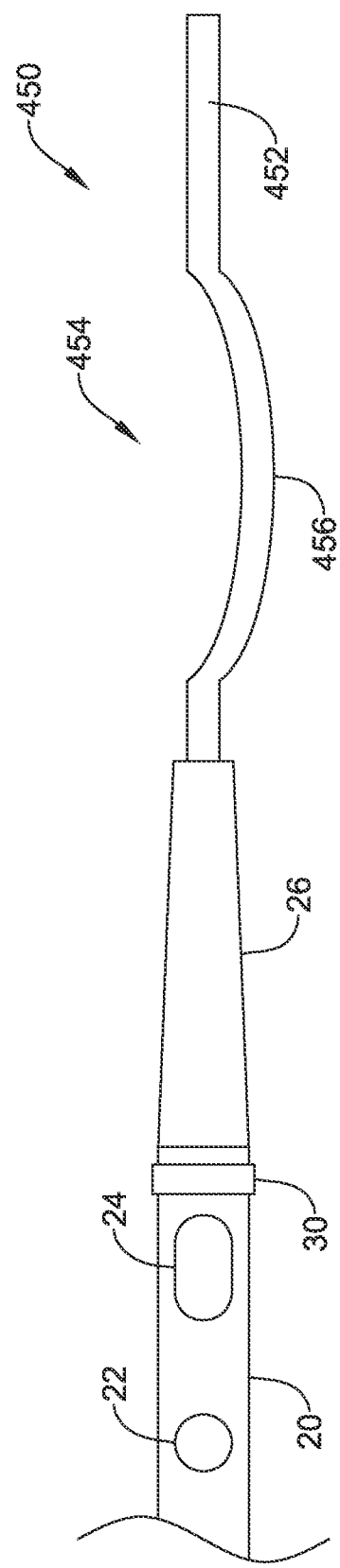
FIG. 27 is a side view of another illustrative accessory device.
Figure 28:
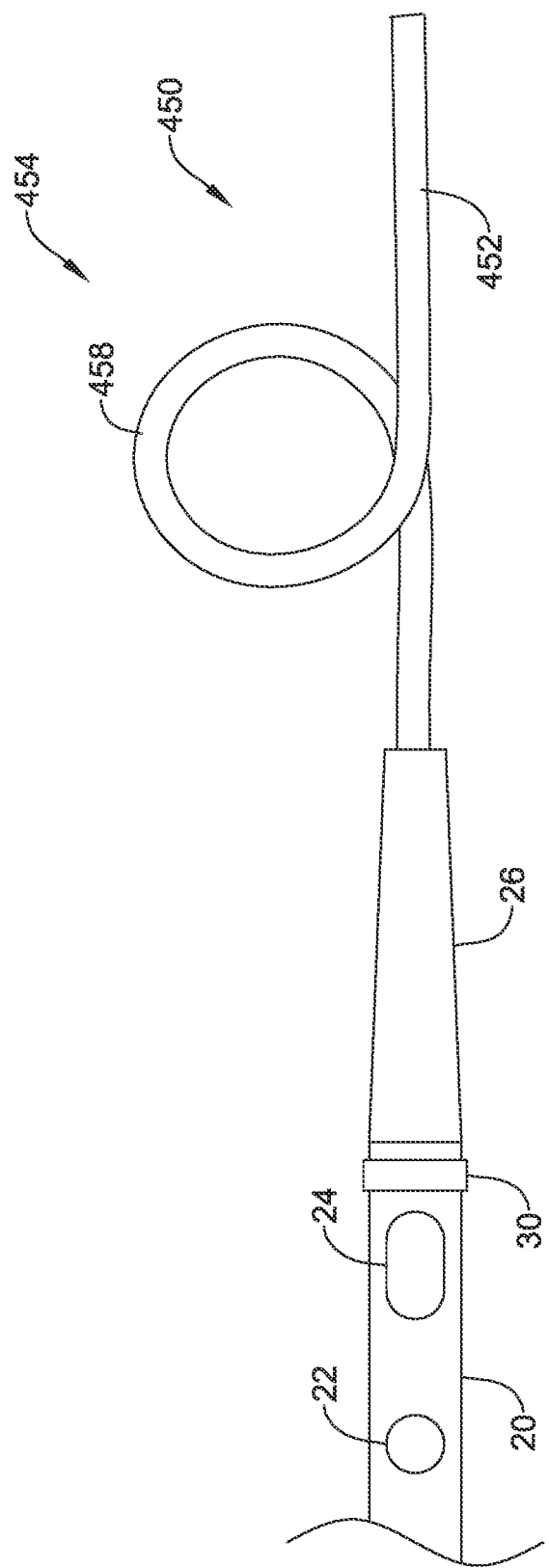
FIG. 28 is a side view of another illustrative accessory device.
Figure 29:
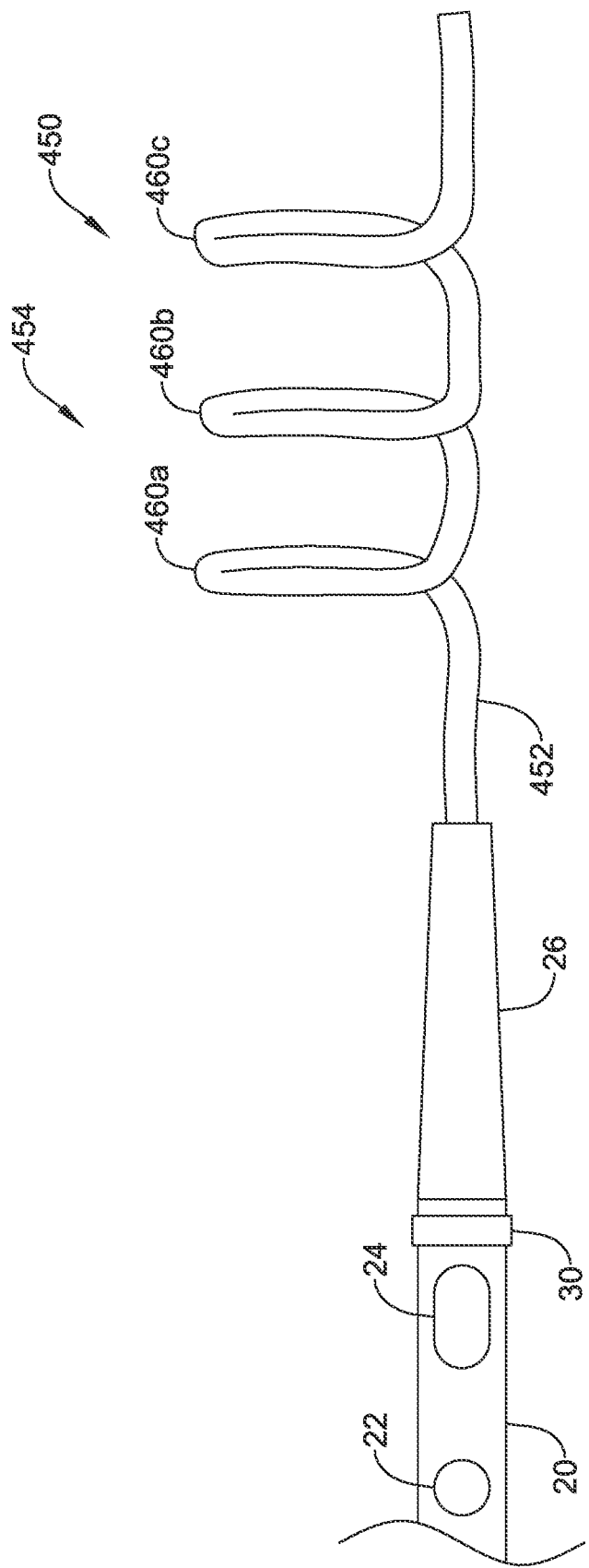
FIG. 29 is a side view of another illustrative accessory device.
Figure 30:
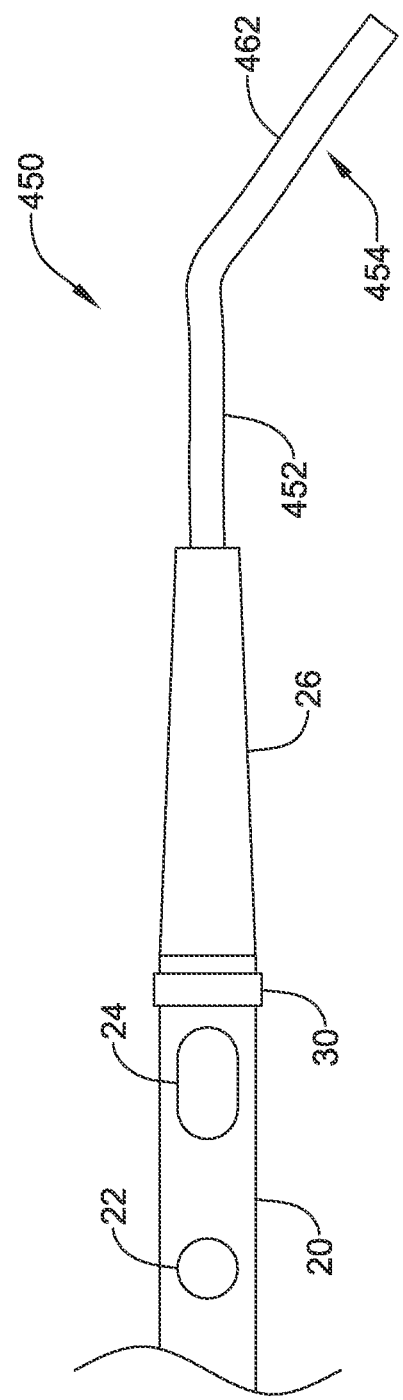
FIG. 30 is a side view of another illustrative accessory device.
Figure 31:
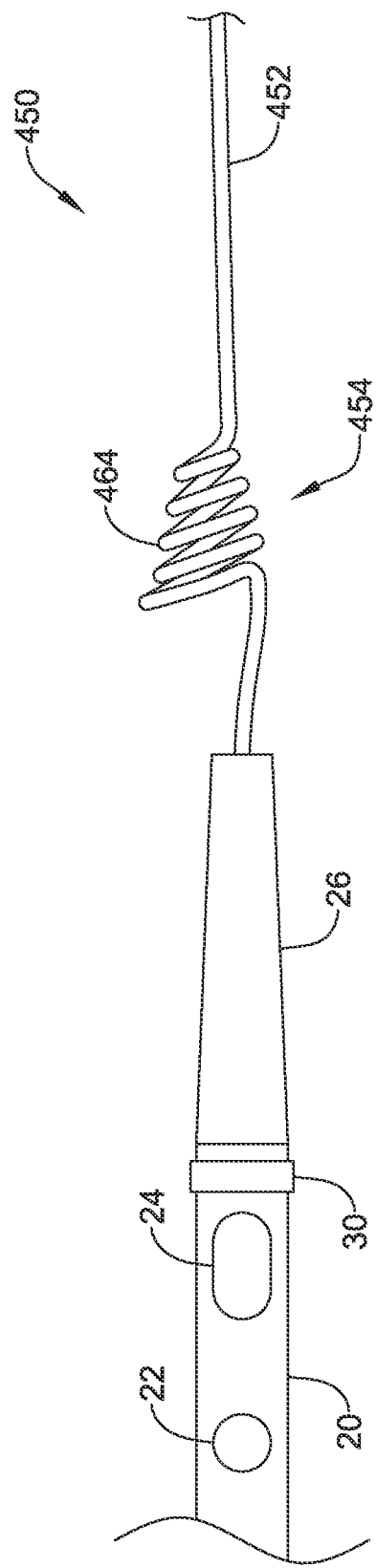
FIG. 31 is a side view of another illustrative accessory device.

FIG. 26 illustrates a side view of another illustrative accessory device 400 that may be used with a thrombectomy catheter, such as the thrombectomy catheter 10 described herein. The accessory device 400 may include a straight or angled (such as the bent guidewire 162 described herein) tubular member or guidewire 402 and an expandable cage 404 extending from a distal end region 406 of the guidewire 402. The guidewire 402 may be similar in form and function to the guidewire 162 described herein. However, the predetermined bend 170 described herein may or may not be present resulting in an angled or straight guidewire, as desired. Alternatively, or additionally, the guidewire 402 may be a tubular member having a lumen extending therethrough. The expandable cage 404 may be slidably disposed through the lumen of the tubular member. The proximal end of the device 400 may be releasably coupled to a control handle, such as the control handle 150 described herein. Use of the control handle 150 may allow the device 400 to be retracted, deployed, and rotated in a controlled manner, although its use is not required.

The cage 404 may comprise a plurality of collapsible struts 408a, 408b, 408c, 408d (collectively, 408). While the cage 404 is illustrated as having four struts, it is contemplated that the cage 404 may include any number of struts 408, such as but not limited one, two, three, four, or more, as desired. In some instances, each strut 408 may be comprised of two or more individual wires (not explicitly shown), although this is not required. In some embodiments, each strut 408 may be formed from a single wire or strut. The struts 408 may be made from stainless steel or a shape memory material such as, but not limited to nitinol. The stiffness of the struts 408 may be varied as desired. In some instances, the struts 408 may be provided with serrations and/or sharp edges to aid in clot maceration. In some embodiments, the outer most part of the struts 408 may remain smooth since this will be the part that may contact the vessel wall and help center the device.

The struts 408 may be evenly spaced or eccentrically spaced as desired. For example, in some cases, the struts 408 may be positioned approximately 90° from one another. It is further contemplated that the cage 404 may be self-expanding or include an actuation mechanism to manually deploy the cage 404. The cage 404 may be collapsible into a delivery configuration which may have a smaller cross-sectional area and a longer length that the expanded cage 404 illustrated in FIG. 26.

The struts 408 may be affixed to one another and/or the guidewire 402 and/or a central shaft 416 at their collective proximal end 420. The distal ends 422a, 422b, 422c, 422d (collectively 422) of the struts 408 may be biased outward in an expanded configuration (shown in FIG. 26). The distal ends 422 may have a protective safety band 418 connected thereto and extending around a perimeter of the distal end of the cage 404. The safety band 418 may be made of a flexible material or structured to have a collapsed configuration to allow it to be collapsed into a reduced profile delivery configuration. A central shaft 416 may be extend longitudinally through a center of the cage 404. A rotatable propeller 410 may be rotationally affixed to the distal end 424 of the central shaft 416. The propeller 410 may include a plurality of blades 412a, 412b, 412c, 412d (collectively, 412). While the propeller 410 is illustrated as having four blades 412, it is contemplated that the propeller 410 may include any number of blades 412, such as but not limited one, two, three, four, or more, as desired. The blades 412 may be configured to draw any clot or debris towards the thrombectomy catheter 10. For example, the pitch and rotational direction of the blades 412 may be configured to draw any clot or debris towards the thrombectomy catheter 10. The propeller 410 may be electrically connected to a motor configured to remain outside the body to drive rotation of the propeller 410.

The accessory guidewire based device 400 with the expandable cage 404 on the distal end may be advanced through the guidewire or aspiration lumen of the thrombectomy catheter 10. The device 400 can be operated in a pecking motion, dragging motion, or manually and/or electrically rotated to help aid in the disruption of the lesion. This may increase removal or shorten a procedure when combined with the evacuative and shearing properties of the thrombectomy catheter 10. Furthermore, the cage 404 may be retracted, rotated, and deployed with a special handle, as described herein with respect to FIGS. 13 and 14. As described herein, the device 400 may also have a bent guidewire 402 to deflect the distal end region of the thrombectomy catheter 10 relative to a longitudinal axis of the catheter tube proximal to the bend in the guidewire 402. Deflecting the distal end region of the catheter 10 may increase the sweep coverage of the distal end region and/or device 400. For example, as the deflection angle increases, the sweep coverage of the distal end region of the catheter 10 and/or guidewire 402 may also increase. Additionally, deflection of the distal end region of the catheter 10 may also bring the inflow window 24 and jets 140a-140n closer to the thrombus to further facilitate removal of the tissue. It is contemplated that the accessory device 400 should not cause any additional hemolysis since the shear rate for blood cells is not exceeded in the arrangement.

FIGS. 27-31 each illustrate a side view of another illustrative accessory device 450 that may be used with a thrombectomy catheter, such as the thrombectomy catheter 10 described herein. The accessory device 450 may include a straight or angled (such as the bent guidewire 162 described herein) tubular member or guidewire 452. It is contemplated that the guidewire 452 may be a solid core wire, a traditional guidewire structure, or a tubular member, as desired. In some instances, the guidewire 452 may be similar in form and function to the guidewire 162 described herein. However, the predetermined bend 170 described herein may or may not be present resulting in an angled or straight guidewire, as desired. The proximal end of the device 450 may be releasably coupled to a control handle, such as the control handle 150 described herein. Use of the control handle 150 may allow the device 450 to be retracted, deployed, and rotated in a controlled manner, although its use is not required.

In some instances, a distal region of the guidewire 452 may have a disruption feature 454 configured to facilitate clot maceration. It is contemplated that the disruption feature 454 may be configured to increase the sweep coverage of the guidewire 452. The disruption feature 454 may take a variety of forms including, but not limited to a bend or curve 456 (FIG. 27), a loop 458 (FIG. 28), a plurality of loops 460 (FIG. 29), an angled tip 462 (FIG. 30), a tapered spiral 464 (FIG. 31), or combinations thereof. These are just examples. Other structures are also envisioned, including but not limited a uniform diameter coil, a coil having varying pitch, a curved tip, etc. The guidewire 452 may be made from stainless steel or a shape memory material such as, but not limited to nitinol. The stiffness of the guidewire 452 may be varied as desired.

The accessory guidewire based device 450 may be advanced through the guidewire or aspiration lumen of the thrombectomy catheter 10. The device 450 can be operated in a pecking motion, dragging motion, or manually and/or electrically rotated to help aid in the disruption of the lesion. This may increase removal or shorten a procedure when combined with the evacuative and shearing properties of the thrombectomy catheter 10. Furthermore, the device 450 may be retracted, rotated, and deployed with a special handle, as described herein with respect to FIGS. 13 and 14. As described herein, the device 450 may also have a bent guidewire 452 to deflect the distal end region of the thrombectomy catheter 10 relative to a longitudinal axis of the catheter tube proximal to the bend in the guidewire 452. It is contemplated that if so provided, the bend may be positioned proximal to the disruption feature. Deflecting the distal end region of the catheter 10 may further increase the sweep coverage of the distal end region of the catheter 10 and/or device 450. For example, as the deflection angle increases, the sweep coverage of the distal end region and/or guidewire 452 may also increase. Additionally, deflection of the distal end region of the catheter 10 may also bring the inflow window 24 and jets 140a-140n closer to the thrombus to further facilitate removal of the tissue. It is contemplated that the accessory device 450 should not cause any additional hemolysis since the shear rate for blood cells is not exceeded in the arrangement.

Figure 32:
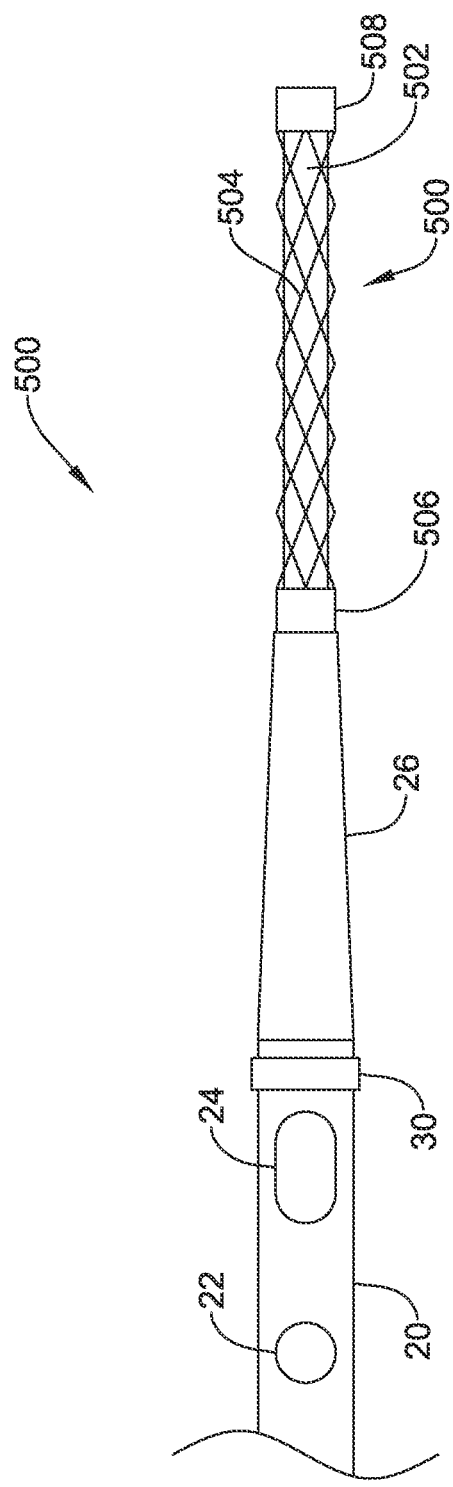
FIG. 32 is a side view of another illustrative accessory device in a first configuration.
Figure 33:
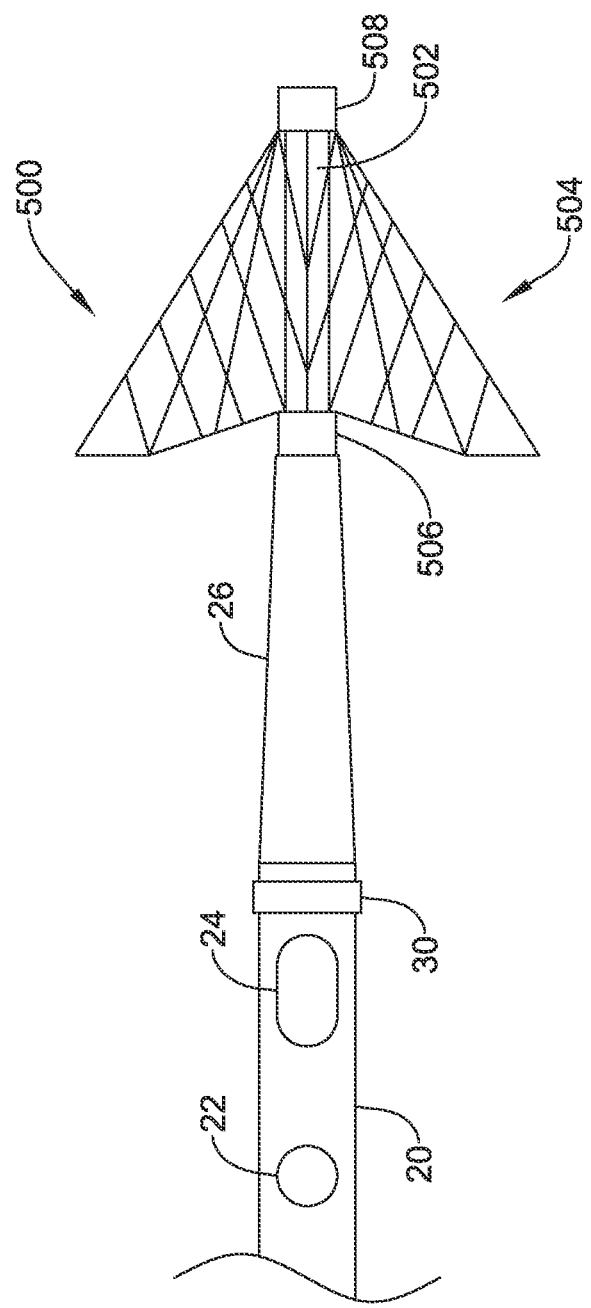
FIG. 33 is another side view of the illustrative accessory device of FIG. 32 in a second configuration.
Figure 34:
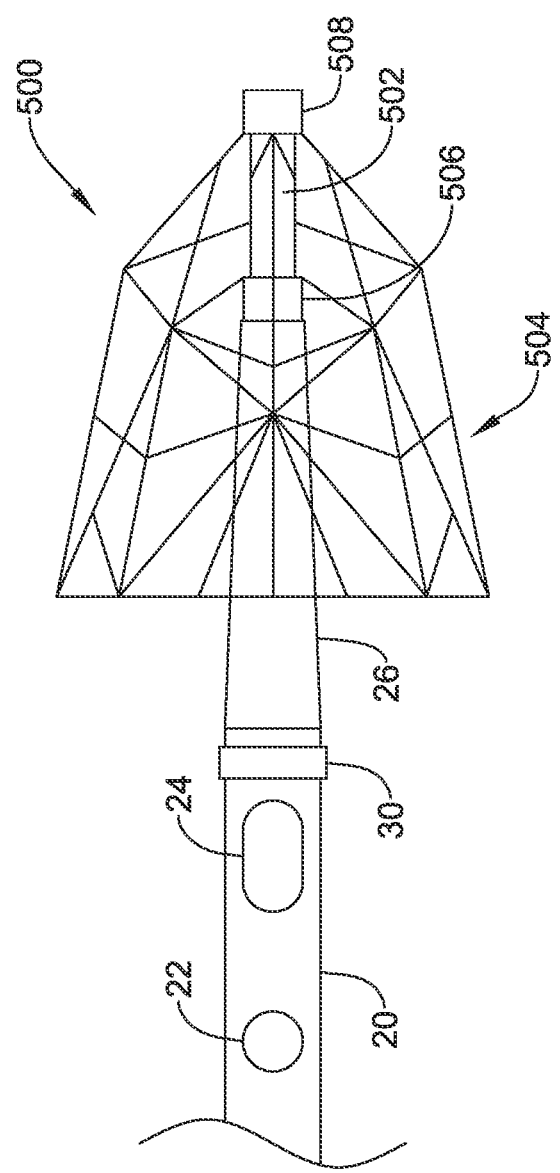
FIG. 34 is another side view of the illustrative accessory device of FIGS. 32 and 33 in a third configuration.

FIGS. 32-34 illustrate another illustrative accessory device 500 that may be used with a thrombectomy catheter, such as the thrombectomy catheter 10 described herein. The accessory device 500 may include a core wire 502 and an expandable cage 504 positioned adjacent to a distal end of the core wire 502. The proximal end of the device 500 may be releasably coupled to a control handle, such as the control handle 150 described herein. Use of the control handle 150 may allow the device 500 to be retracted, deployed, and rotated in a controlled manner, although its use is not required.

The cage 504 may be formed from a laser cut nitinol tube, although other materials may also be used. The tube may be cut to form a lattice or woven type structure. Alternatively, the cage 504 may be formed from a plurality of wound or woven filaments. The cage 504 may be coupled at its distal end to the distal end of the core wire 502 at a distal collar 508. A proximal collar 506 may be positioned on or adjacent to the tip 26 of the thrombectomy catheter 10. The device 500 may be advanced with the thrombectomy catheter 10 or may be advanced through a lumen of the thrombectomy catheter 10 after the catheter 10 has been positioned adjacent to the lesion, as desired. In some instances, the device 500 may be formed as a component of the catheter 10. It is contemplated that the cage 504 may be configured to be advanced distally beyond the distal end of the catheter 10 or may be formed as a distal extension to the catheter 10.

The cage 504 may have a collapsed, low-profile, delivery configuration, as shown in FIG. 32. Once the device 500 is positioned adjacent to the lesion, the core wire 502 may be proximally retracted to expand the cage 504, as shown in FIG. 33. Additional proximal actuation of the core wire 502 may fully expand the cage 504, as shown in FIG. 34. It is further contemplated that proximal actuation of the core wire 502 may also result in proximal movement of the cage 504. This may position the cage 504 over the inflow window 24. It is contemplated that the cage 504 may break up the lesion(s) near the window 24 to allow for easier debris removal.

The device 500 can be operated in a pecking motion, dragging motion, or manually and/or electrically rotated to help aid in the disruption of the lesion. This may increase removal or shorten a procedure when combined with the evacuative and shearing properties of the thrombectomy catheter 10. Furthermore, the cage 504 may be retracted, rotated, and deployed with a special handle, as described herein with respect to FIGS. 13 and 14. It is contemplated that the accessory device 500 should not cause any additional hemolysis since the shear rate for blood cells is not exceeded in the arrangement.

Figure 35A:
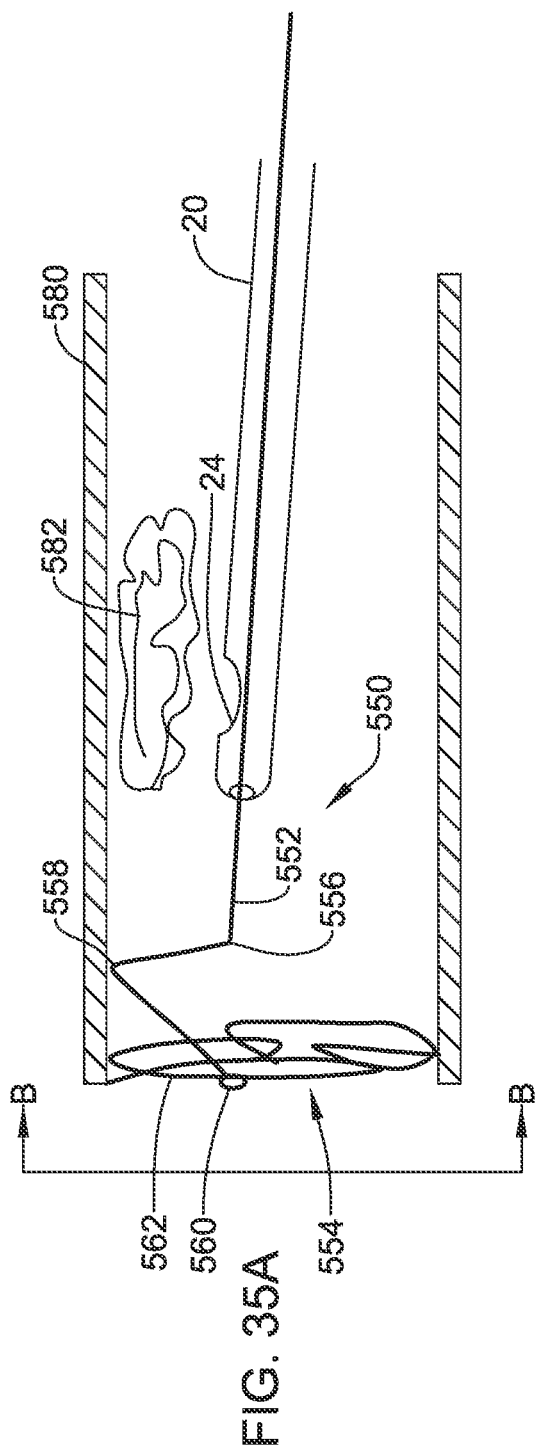
FIG. 35A is a side view of another illustrative accessory device.
Figure 35B:
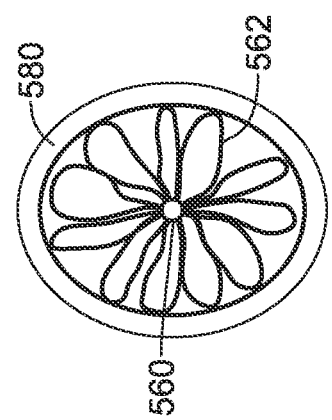
FIG. 35B is an end view of the illustrative accessory device of FIG. 35A.

FIG. 35A illustrates a side view of another illustrative accessory device 550 that may be used with a thrombectomy catheter, such as the thrombectomy catheter 10 described herein. FIG. 35B illustrates a distal end view of the accessory device 550. The device 550 is shown in FIG. 35A disposed within a vessel 580 (shown in cross-section) having a lesion 582. The accessory device 550 may include a guidewire 552 and a rotatable cage 554 positioned adjacent to a distal end of the core wire 502. The proximal end of the device 550 may be releasably coupled to control handle, such as control handle 150 described herein. Use of the control handle 150 may allow the device 550 to be retracted, deployed, and rotated in a controlled manner.

The guidewire 552 may include a first bend 556 configured to bias a portion of the device 550 towards a wall of the vessel 580 and/or the lesion 582. The guidewire 552 may include a second bend 558 configured to direct the cage 554 towards the center of vessel 580. It is further contemplated that the structure of the guidewire 552 may prevent the catheter 10 from bouncing off of the lesion 582. The guidewire 552 may be attached to the rotatable cage 554 at a rotating joint 560 such that the cage 554 is articulated as the guidewire 552 is manually torqued. The roatating joint 560 may be, for example, a ball and socket or hinge. A distal end view of the cage 554 is illustrated in FIG. 35B. The cage 554 may include a plurality of petal-like strands 562. In the expanded configuration, the cage 554 may be postioned in a plane extending generally orthogonal to a longitudinal axis of the vessel. The cage 554 may be formed from one or more of wound or woven filaments. The cage 554 may act as a filter to help prevent debris from the lesion 582 from being swept downstream.

It is further contemplated that the cage 554 may be self-expanding or include an actuation mechanism to manually deploy the cage 554. The cage 554 may be collapsible into a delivery configuration which may have a smaller cross-sectional area and a longer length than the expanded cage 554 illustrated in FIG. 35A.

The materials that can be used for the various components of the catheter, guidewires, accessory device, and/or other devices disclosed herein may include those commonly associated with medical devices. For simplicity purposes, the following discussion makes reference to accessory devices and their related components. However, this is not intended to limit the devices and methods described herein, as the discussion may be applied to other similar devices, tubular members and/or components of tubular members or devices disclosed herein.

The various components of the devices/systems disclosed herein may include a metal, metal alloy, polymer (some examples of which are disclosed herein), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In at least some embodiments, portions or all of the accessory devices and their related components may be doped with, made of, or otherwise include a radiopaque to material. Radiopaque materials are understood to be materials capable of producing a relatively bright image on a fluoroscopy screen or another imaging technique during a medical procedure. This relatively bright image aids the user of the accessory devices and their related components in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the accessory devices and their related components to achieve the same result.

EXAMPLES

In a first example, a thrombectomy catheter may comprise a catheter body extending from a catheter proximal portion to a catheter distal portion and including a catheter lumen extending between the proximal portion and the distal portion, a high pressure tube extending through the catheter lumen from the catheter proximal portion toward the catheter distal portion, the high pressure tube configured for communication with a fluid source near the catheter proximal portion, a fluid jet emanator in communication with the high pressure tube, the fluid jet emanator having at least one jet orifice for directing at least one fluid jet from said fluid jet emanator through the catheter lumen, an outflow orifice located along a catheter perimeter of the catheter distal portion, an entrainment inflow orifice positioned along the catheter distal portion, and an accessory device disposed within the catheter lumen.

Alternatively or additionally to any of the examples above, in another example, the accessory device may comprise a guidewire having proximal end portion and a distal end portion.

Alternatively or additionally to any of the examples above, in another example, the guidewire may comprise an elongate core wire having a coil disposed over a length of the core wire adjacent to a distal end of the core wire.

Alternatively or additionally to any of the examples above, in another example, the proximal portion of the guidewire may extend along a longitudinal axis and the distal portion of the guidewire may be configured to extend at an angle to the longitudinal axis.

Alternatively or additionally to any of the examples above, in another example, the angle may be in the range of 1 to 90°.

Alternatively or additionally to any of the examples above, in another example, the angle may be in the range of 10 to 60°.

Alternatively or additionally to any of the examples above, in another example, the angle may be in the range of 10 to 30°.

Alternatively or additionally to any of the examples above, in another example, the angle may be in the range of 15 to 25°.

Alternatively or additionally to any of the examples above, in another example, the angle may be approximately 20°.

Alternatively or additionally to any of the examples above, in another example, the guidewire may comprise a bent portion disposed between the proximal end portion and the distal end portion of the guidewire.

Alternatively or additionally to any of the examples above, in another example, the bent portion of the guidewire may be configured to deflect a portion of the catheter body positioned distal to the bend portion.

Alternatively or additionally to any of the examples above, in another example, when the bend portion is positioned at a first longitudinal location within the catheter lumen, the thrombectomy catheter may have a first diametrical sweep coverage and when the bend portion is positioned at a second longitudinal location within the catheter lumen, the second location proximal to the first location, the thrombectomy catheter may have a second diametrical sweep coverage greater than the first diametrical sweep coverage.

Alternatively or additionally to any of the examples above, in another example, the accessory device may be slidably disposed within the catheter lumen.

Alternatively or additionally to any of the examples above, in another example, the accessory device may be rotationally disposed within the catheter lumen.

Alternatively or additionally to any of the examples above, in another example, the thrombectomy catheter may further comprise an expandable cage positioned adjacent to a distal end of the accessory device.

Alternatively or additionally to any of the examples above, in another example, the expandable cage may be a cut tube.

Alternatively or additionally to any of the examples above, in another example, the expandable cage may comprise a plurality of strands extending from a proximal end of the cage to a distal end of the cage.

Alternatively or additionally to any of the examples above, in another example, each strand of the plurality of strands may be formed from two or more wires.

Alternatively or additionally to any of the examples above, in another example, a proximal end and a distal end of each strand of the plurality of strands may be coupled to the accessory device.

Alternatively or additionally to any of the examples above, in another example, the expandable cage may be configured to move between a collapsed configuration to an expanded configuration.

Alternatively or additionally to any of the examples above, in another example, the expandable cage may be self-expanding.

Alternatively or additionally to any of the examples above, in another example, the thrombectomy catheter may further comprise an actuation mechanism, the actuation mechanism may be configured to move the expandable cage between the collapsed configuration and the expanded configuration.

Alternatively or additionally to any of the examples above, in another example, in the expanded configuration, the strands may be configured to curve away from a longitudinal axis of the accessory device along a length of the strands such that a cross-sectional diameter of the cage in the expanded configuration is larger than a cross-sectional diameter of the cage in the collapsed configuration.

Alternatively or additionally to any of the examples above, in another example, in the expanded configuration, each strand of the plurality of strands may have a generally helically shape such that a distal end of each strand is circumferentially offset form a proximal end of the strand.

Alternatively or additionally to any of the examples above, in another example, the thrombectomy catheter may further comprise a control handle releasably secured adjacent to a proximal end of the accessory device.

Alternatively or additionally to any of the examples above, in another example, the control handle may comprise a body portion, a slide portion, and a collet portion.

Alternatively or additionally to any of the examples above, in another example, the collet portion may be configured to be releasably secured to the accessory device.

Alternatively or additionally to any of the examples above, in another example, the body portion and the collet portion may be configured to actuate relative to the slide portion.

Alternatively or additionally to any of the examples above, in another example, the body portion and the collet portion may be configured to actuate along a longitudinal axis of the control handle.

Alternatively or additionally to any of the examples above, in another example, actuating the body portion and the collet portion may move the handle between an extended configuration and a retracted configuration.

Alternatively or additionally to any of the examples above, in another example, actuating the body portion and the collet portion may result in proximal and/or distal movement of the accessory device.

Alternatively or additionally to any of the examples above, in another example, the control handle may be configured to rotate independent of the catheter body.

Alternatively or additionally to any of the examples above, in another example, the accessory device may be configured to rotate with rotation of the control handle.

Alternatively or additionally to any of the examples above, in another example, the outflow orifice may be configured to generate a jet stream out of the catheter body with the at least one fluid jet, the jet stream including first and second stream portions.

Alternatively or additionally to any of the examples above, in another example, the entrainment inflow orifice may be configured to receive the jet stream first portion and direct the jet stream first portion and entrained particulate toward the outflow orifice.

In another illustrative example, an accessory device for use with a medical device may comprise an elongated core wire having proximal portion, a distal portion, and a curved portion disposed between the proximal portion and the distal portion, wherein the proximal portion of the core wire extends along a longitudinal axis and the distal portion of the core wire extends from the curved portion at an angle to the proximal portion.

Alternatively or additionally to any of the examples above, in another example, the core wire may be configured to be slidably and/or rotationally disposed within a lumen of the medical device.

Alternatively or additionally to any of the examples above, in another example, the accessory device may be configured to deflect distal end region of the medical device from a longitudinal axis of the medical device.

Alternatively or additionally to any of the examples above, in another example, an amount of deflection of the distal end region may vary with a longitudinal location of the curved portion of the core wire.

Alternatively or additionally to any of the examples above, in another example, the angle may be in the range of 1 to 45°.

Alternatively or additionally to any of the examples above, in another example, the accessory device may further comprise an expandable cage positioned adjacent the distal end portion of the core wire.

Alternatively or additionally to any of the examples above, in another example, the expandable cage may comprise a plurality of struts extending from a proximal end of the cage to a distal end of the cage.

Alternatively or additionally to any of the examples above, in another example, each strut of the plurality of struts may be formed from two or more wires.

Alternatively or additionally to any of the examples above, in another example, a proximal end and a distal end of each strut of the plurality of struts may be coupled to the accessory device.

Alternatively or additionally to any of the examples above, in another example, the expandable cage may be configured to move between a collapsed configuration to an expanded configuration.

Alternatively or additionally to any of the examples above, in another example, in the expanded configuration, the struts may be configured to curve away from a longitudinal axis of the accessory device along a length of the struts such that a cross-sectional diameter of the cage in the expanded configuration maybe larger than a cross-sectional diameter of the cage in the collapsed configuration.

Alternatively or additionally to any of the examples above, in another example, in the expanded configuration, each strut of the plurality of struts may have a generally helically shape such that a distal end of each strut is circumferentially offset form a proximal end of said strut.

Alternatively or additionally to any of the examples above, in another example, the accessory device may further comprise a control handle releasably coupled adjacent to a proximal end of the core wire.

In another example, an accessory device for use with a medical device may comprise an elongated member having proximal portion and a distal portion an expandable cage comprising a plurality of longitudinally extending struts, the expandable cage disposed adjacent to the distal portion of the elongated member such that a length of the distal portion extends distally beyond a distal end of the expandable cage.

Alternatively or additionally to any of the examples above, in another example, the elongated member may be configured to be slidably and/or rotationally disposed within a lumen of the medical device.

Alternatively or additionally to any of the examples above, in another example, the elongated member may comprise a tubular member.

Alternatively or additionally to any of the examples above, in another example, the struts of the expandable cage may be formed by removing material from the tubular member.

Alternatively or additionally to any of the examples above, in another example, the expandable cage may be configured to move between a collapsed configuration to an expanded configuration.

Alternatively or additionally to any of the examples above, in another example, in the expanded configuration, the struts may be configured to curve away from a longitudinal axis of the accessory device along a length of the struts such that a cross-sectional diameter of the cage in the expanded configuration may be larger than a cross-sectional diameter of the cage in the collapsed configuration.

Alternatively or additionally to any of the examples above, in another example, in the expanded configuration, each strut of the plurality of struts may have a generally helically shape such that a distal end of each strut is circumferentially offset form a proximal end of said strut.

Alternatively or additionally to any of the examples above, in another example, the elongated member may comprise a solid core wire.

Alternatively or additionally to any of the examples above, in another example, each strut of the plurality of struts may be formed from two or more wires.

Alternatively or additionally to any of the examples above, in another example, a proximal end and a distal end of each strut of the plurality of struts may be coupled to the core wire.

Alternatively or additionally to any of the examples above, in another example, the expandable cage may be configured to move between a collapsed configuration to an expanded configuration.

Alternatively or additionally to any of the examples above, in another example, in the expanded configuration, the struts may be configured to curve away from a longitudinal axis of the accessory device along a length of the struts such that a cross-sectional diameter of the cage in the expanded configuration may be larger than a cross-sectional diameter of the cage in the collapsed configuration.

Alternatively or additionally to any of the examples above, in another example, in the expanded configuration, each strut of the plurality of struts may have a generally helically shape such that a distal end of each strut is circumferentially offset form a proximal end of said strut.

Alternatively or additionally to any of the examples above, in another example, the accessory device may further comprise a control handle releasably coupled adjacent to a proximal end of the elongated member.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A thrombectomy catheter, comprising:
   a catheter body extending from a proximal portion to a distal portion and including a catheter lumen extending between the proximal portion and the distal portion;
   a high pressure tube extending through the catheter lumen from the proximal portion of the catheter body toward the distal portion of the catheter body, the high pressure tube configured for communication with a fluid source near the proximal portion of the catheter body;
   a fluid jet emanator in communication with the high pressure tube, the fluid jet emanator having at least one jet orifice for directing at least one fluid jet from said fluid jet emanator through the catheter lumen;
   an outflow orifice located along a catheter perimeter of the distal portion of the catheter body;
   an entrainment inflow orifice positioned along the distal portion of the catheter body; and
   an accessory device disposed within the catheter lumen, the accessory device comprising:
      an elongated member having a proximal portion and a distal portion; and
      an expandable cage configured to move between a collapsed configuration and an expanded configuration, the expandable cage comprising a plurality of longitudinally extending struts comprising a plurality of strands, the expandable cage disposed adjacent to the distal portion of the elongated member such that a length of the distal portion extends distally beyond a distal end of the expandable cage; wherein when in the expanded configuration, each strand of the plurality of strands has a generally helically shape such that a distal end of each strand is circumferentially offset from a proximal end of a same strand.

2. The thrombectomy catheter of claim 1, wherein the expandable cage is self-expanding.

3. The thrombectomy catheter of claim 1, further comprising an actuation mechanism, the actuation mechanism configured to move the expandable cage between the collapsed configuration and the expanded configuration.

4. The thrombectomy catheter of claim 1, wherein the expandable cage is a cut tube.

5. The thrombectomy catheter of claim 1, wherein each strand of the plurality of strands is formed from two or more wires.

6. The thrombectomy catheter of claim 1, wherein a proximal end and a distal end of each strand of the plurality of strands are coupled to the elongated member.

7. The thrombectomy catheter of claim 1, wherein the elongated member comprises a tubular member.

8. The thrombectomy catheter of claim 7, wherein the struts of the expandable cage are formed by removing material from the tubular member.

9. The thrombectomy catheter of claim 1, wherein when in the expanded configuration, the plurality of strands are configured to curve away from a longitudinal axis of the accessory device along a length of the plurality of strands such that a cross-sectional diameter of the expandable cage in the expanded configuration is larger than a cross-sectional diameter of the expandable cage in the collapsed configuration.

10. The thrombectomy catheter of claim 1, further comprising a control handle releasably secured adjacent to a proximal end of the accessory device.

11. The thrombectomy catheter of claim 1, wherein the accessory device is slidably and/or rotationally disposed within the catheter lumen.

12. A thrombectomy catheter, comprising:
a catheter tube extending from a proximal portion to a distal portion and including a catheter lumen extending between the proximal portion and the distal portion;
a high pressure tube extending through the catheter lumen from the proximal portion of the catheter tube toward the distal portion of the catheter tube, the high pressure tube configured for communication with a fluid source near the proximal portion of the catheter tube;
a fluid jet emanator in communication with the high pressure tube, the fluid jet emanator having at least one jet orifice for directing at least one fluid jet from said fluid jet emanator through the catheter lumen;
an outflow orifice located along a catheter perimeter of the distal portion of the catheter tube;
an entrainment inflow orifice positioned along the distal portion of the catheter tube;
an accessory device disposed within the catheter lumen, the accessory device comprising:
an elongated member having a proximal portion and a distal portion; and
an expandable cage comprising a plurality of longitudinally extending struts, the expandable cage disposed adjacent to the distal portion of the elongated member such that a length of the distal portion extends distally beyond a distal end of the expandable cage, wherein when in an expanded configuration, each strut of the plurality of struts has a generally helically shape such that a distal end of each strut is circumferentially offset from a proximal end of a same strut; and
a handle releasably secured to the elongated member adjacent to a proximal portion of the elongated member and configured to rotate independent of the catheter tube.

13. The thrombectomy catheter of claim 12, wherein the expandable cage comprises a plurality of strands extending from a proximal end of the expandable cage to a distal end of the expandable cage.

14. The thrombectomy catheter of claim 13, wherein a proximal end and a distal end of each strand of the plurality of strands are coupled to the elongated member.

15. The thrombectomy catheter of claim 12, wherein the elongated member comprises a tubular member.

16. The thrombectomy catheter of claim 15, wherein the struts of the expandable cage are formed by removing material from the tubular member.

17. A thrombectomy catheter, comprising:
a catheter tube extending from a proximal portion to a distal portion and including a catheter lumen extending between the proximal portion and the distal portion;
a high pressure tube extending through the catheter lumen from the proximal portion of the catheter tube toward the distal portion of the catheter tube, the high pressure tube configured for communication with a fluid source near the proximal portion of the catheter tube;
a fluid jet emanator in communication with the high pressure tube, the fluid jet emanator having at least one jet orifice for directing at least one fluid jet from said fluid jet emanator through the catheter lumen;
an outflow orifice located along a catheter perimeter of the distal portion of the catheter tube;
an entrainment inflow orifice positioned along the distal portion of the catheter tube;
an accessory device disposed within the catheter lumen, the accessory device comprising:
an elongated member having proximal portion and a distal portion; and
an expandable cage comprising a plurality of longitudinally extending struts, the expandable cage configured to move between a collapsed configuration and an expanded configuration and disposed adjacent to the distal portion of the elongated member such that a length of the distal portion extends distally beyond a distal end of the expandable cage, wherein when in the expanded configuration, each strut of the plurality of struts has a generally helically shape such that a distal end of each strut is circumferentially offset from a proximal end of a same strut; and
a handle releasably secured to the elongated member adjacent to the proximal portion of the elongated member.

* * * * *